United States Patent [19]

Riviello et al.

[11] Patent Number: 5,403,451

[45] Date of Patent: Apr. 4, 1995

[54] METHOD AND APPARATUS FOR PULSED ELECTROCHEMICAL DETECTION USING POLYMER ELECTROACTIVE ELECTRODES

[76] Inventors: John M. Riviello, 2430 Paul Minnie Ave., Santa Cruz, Calif. 95062; Gordon Wallace, 35 Francis Street, Wollongong NSW, Australia; Omowunmi A. Sadik, c/o Dr PO Ogunbona, PO Box 19, Keiraville NSW 2500, Australia

[21] Appl. No.: 206,136

[22] Filed: Mar. 4, 1994

[30] Foreign Application Priority Data

Mar. 5, 1993 [AU] Australia ................. PL7664

[51] Int. Cl.$^6$ ............................................. G01N 27/26
[52] U.S. Cl. ............... 204/153.1; 204/153.12; 204/403; 204/409; 204/412; 204/434; 435/7.1; 435/7.8; 435/7.93
[58] Field of Search ................ 204/163.1, 153.12, 403, 204/409, 412, 434; 435/7.1, 7.8, 7.93

[56] References Cited

U.S. PATENT DOCUMENTS

| | | | |
|---|---|---|---|
| 4,321,322 | 3/1982 | Ahnell | 204/153.12 |
| 4,939,924 | 7/1990 | Johnson et al. | 204/402 |
| 5,312,762 | 5/1994 | Guiseppi-Elie | 204/403 |

OTHER PUBLICATIONS

"Doping-dedoping of Polypyrrole: A study using current measuring and resistance-meaning techniques" by R. John and G. G. Wallace, J. Electroanal. Chem. 354 (1993) pp. 145-160.

"Molecular Recognition Using Conducting Polymers: Basis of an Electro-Chemical Sensing Technology", by P. R. Teasdale and G. G. Wallace, Analyst, Apr. 1993 vol. 118, pp. 329-334.

"Pulsed amperometric detections of proteins using antibody containing conducting polymers", by O. A. Sadik and G. G. Wallace, Analytica Chimica Acta (1993) pp. 209-212.

"Effect of Polymer Composition on the Detection of Electroinactive Species Using Conductive Polymers", by Omowunmi A. Sadik and Gordon G. Wallace, Electroanalysis 5 (1993) pp. 555-563.

"Polypyrrole Electrode as a Detector for Electroinactive Anions by Flow Injection Analysis" by Toshihito Ikariyama and William R. Heineman, American Chemical Society 1986.

"Flow Injection Analysis of Electroinactive Anions at a Polyaniline Electrode" by Jiannong and Richard P. Baldwin, Analytical Chemistry 1988, 60 pp. 1979-1982.

*Primary Examiner*—John Niebling
*Assistant Examiner*—Bruce F. Bell
*Attorney, Agent, or Firm*—Flehr, Hohohbach, Test, Albritton & Herbert

[57] ABSTRACT

In a first embodiment, a target analyte in solution is detected by exposing the solution to an electrode that includes a conducting electroactive polymer to which a periodic alternating voltage is coupled. Upon exposure to the analyte, an electrode characteristic is varied, which variation is detected by measuring electrode current as a function of time and as a function of the periodic alternating voltage. The alternating voltage waveform has an oxidizing time period and a reduction time period, which periods and waveform duty cycle may be controlled to enhance electrode sensitivity, selectivity, and to substantially eliminate electrode fouling and data hysteresis. In a second embodiment, a receptor is bound to the electrode, to which is coupled an alternating voltage waveform that permits a mating target substance to reversibly bind to the receptor such that measurement of electrode current provides a measure of such reversible binding. The second embodiment is especially useful for detecting antibodies, antigens, haptens, DNA, RNA, and enzymes. Either embodiment may be used for detection in flow-through electrochemical cells, flow injection analysis, liquid, and ion chromatography, as well as in capillary electrophoresis.

15 Claims, 12 Drawing Sheets

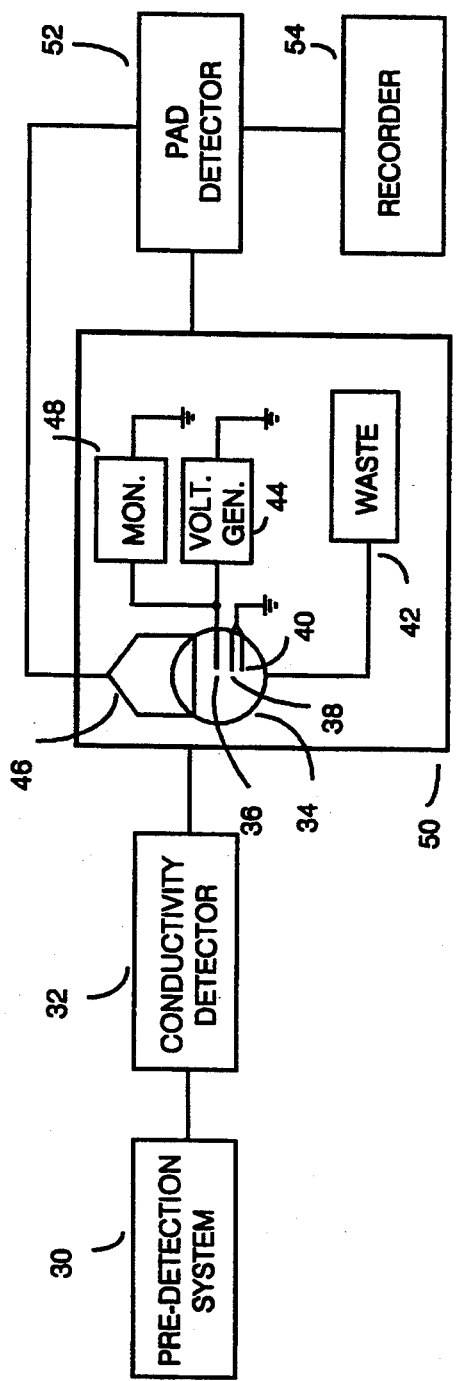
FIG. 2A
FIG. 2C
FIG. 2B

METHOD AND APPARATUS FOR PULSED ELECTROCHEMICAL DETECTION USING POLYMER ELECTROACTIVE ELECTRODES

FIELD OF THE INVENTION

The invention relates to methods and devices for detecting target analytes and for detecting biological interactions such as antibody-antigen attachments using electrochemical electrode sensors, and more particularly to methods and devices using electrochemical electrode sensors that are not fouled during detection.

BACKGROUND OF THE INVENTION

It is known in the art to use electrochemical electrode sensors for detection in solution of analytes in a solution, including electro-inactive analytes. It is also known to use such sensors for in solution detection of attachment between antibody-antigen pairs, between receptors and ligands, proteins, enzymes, electrocatalysts and metal complexing groups. Conducting electroactive polymers ("CEP's") have shown promise as electrochemical sensor electrodes in such applications. In fabricating such sensor electrodes, a conductive inert metal electrode is treated with a CEP such as polypyrrole, polythiophene, or polyaniline. After fabrication, the CEP becomes the active component of the resultant electrochemical sensor.

For reasons of electrode stability and reproducibility, the conducting polymer coating is applied to the metal electrode by electro-deposition or electropolymerization, often using potentiodynamic, potentiostatic, and galvanostatic techniques. Alternatively, a monomer solution in an appropriate solvent can be applied to the metal electrode surface and then evaporated. Because formation of CEP electrodes is known in the art, further details are not presented herein.

FIGS. 1A and 1B depict generic systems that use CEP electrodes for detection, wherein a solution 2 is exposed to a CEP working electrode 4, as well as to a reference electrode 6 and a so-called counter-electrode 8. Generally the reference electrode is coupled to a reference node, preferably ground, and the counter-electrode is electrically coupled to the same node. In FIGS. 1A and 1B, solution 2 is shown as possibly containing target analytes of interest 10 (which analytes may be relatively electro-inactive), and/or other targets 12 that can matingly connect with appropriate receptors 14 affixed to the CEP electrode 4.

The attachment of receptors or ligands 14 to the outer surface of the CEP electrode is known in the art. Receptors 14 that have an attraction affinity targets 12 can include antigens (in which case targets 12 are antibodies), antibodies (in which case targets 12 are antigens), enzymes, proteins, among others.

In the configuration of FIG. 1A, a variable current source 16 is coupled to the CEP electrode 4, and the voltage between the CEP electrode and the reference electrode is measured with a voltmeter (or other apparatus) 18. Typically the current source 16 is slowly varied, and voltmeter reading are recorded. This type of measurement configuration is often referred to as potentiometric.

By contrast, FIG. 1B depicts a so-called amperometric configuration, wherein a variable voltage source 18' is coupled between the CEP electrode and the reference electrode, and current through the CEP electrode is monitored, as with an current meter 16'. Generally, the voltage provided by source 18 is slowly varied or swept (by varying a potentiometer, which is not shown), and current readings are recorded.

CEPs can be electrochemically switched from an oxidized form to a reduced form upon incorporation of a suitable counter-ion during synthesis. When a counter-ion attaches or "hooks" to the CEP, the CEP is said to be doped or oxidized, and when the counter-ion detaches, the CEP is said to be undoped or reduced. By varying the electrical environment to which the CEP is subjected, a neutral, a doped or an undoped state can be made to occur. For example, attachment can occur when a counter-ion is necessary to satisfy a net positive charge on the so-called backbone of the CEP, and detachment can result when there is no longer any need to satisfy the positive net charge on the backbone.

As a CEP electrode incorporates and expels ionic species while switching from an oxidized form to a reduced form, useful analytical signals can be produced. For example, it has long been suggested by Heineman et al. that a CEP may be undoped at a cathodic potential, but redoped when returned to an anodic potential in the presence of an easily incorporated anion analyte, for example phosphate or nitrate. See Y. Ikarayama, C. Caliastsatos, W. R. Heineman, S. Yamanchi, Sens. Act. 12 (1987), 455; Y. Ikarayama, W. R. Heineman, Anal. Chem. 58 (1986) 1803.

Although the precise mechanics of the phenomenon are not completely understood, a counter-ion incorporated during synthesis can have a dramatic effect on the CEP properties, including conductivity, electrochemical switching potential as well as the ion exchange selectivity series.

For example, in FIG. 1A, attachment of an appropriate analyte 10 to the CEP electrode 4 under appropriate bias conditions set by current source 16 can measurably alter the different voltage measured by volt meter 18. By the same token, analyte attachment to the CEP electrode in FIG. 1B under appropriate bias conditions determined by voltage source 18' can alter current flow measured by current meter 16'. Likewise, attraction of suitable targets to receptors 14 in either configuration can also result in a useful analytical signal.

Antigens and antibodies can provide an interaction selectivity, but unfortunately it is difficult in the prior art to generate a meaningful, reproducible analytical signal in response to such interaction. When detecting antigen-antibody attraction, the measurable current or voltage resulting from attraction appears not to be due to any antigen-antibody reaction product. Instead, it is believed that the nature of the CEP itself is changed by the on or off condition of the counter-ion. These problems in attempting to sense a useful interaction signal seem to arise from the lack of a Faradaic (e.g., electron transfer) signal and from the irreversible nature of the antibody-antigen process itself.

The prior art has tried to overcome these measurement problems using potential measurements, indirect amperometric immunoassay techniques, and direct measurements to sense changes in the capacitive nature of the sensor surface after an antibody-antigen interaction. Unfortunately, these procedures are time consuming because of long equilibration times, and/or the multi-step procedures required. Further, the antibody-containing surface must be regenerated chemically to reverse the antibody-antigen interaction.

Antibodies may readily be incorporated into CEPs during synthesis to promote specific reactions with the corresponding antigen. The use of alternating current (AC) voltammetry can provide adequate sensitivity, but reproducibility and the ability to reuse the working electrodes are lacking.

FIG. 1C depicts a cyclic voltammogram ("CV") that is typically produced by the configuration of FIG. 1B, wherein a single sweep is depicted. The data in FIG. 1C is typical of experiments run in a solution of sodium octane sulfonate, wherein the analyte cation will be sodium. Typically voltage source 18' in FIG. 1B is slowly swept at the rate of perhaps 20 mV/second, which means nearly 1.5 minutes are required to sweep 1.6 VDC and generate the data shown in FIG. 1C.

With reference to FIG. 1B and FIG. 1C, the CEP initially is neutral. Let power source 18' initially be about 0 V, whereupon the CEP may be considered to be neutral, or substantially unoxidized. As the voltage sweeps positively (leftwards) to say +0.6 V (e.g., 600 mV), the CEP becomes positively charged (oxidized). To preserve charge balance, this positive charge requires neutralization from negative charges (ions) in the surrounding solution. These ions become incorporated into the CEP structure, and at point B, the current increases as the CEP is fully incorporated (doped) with anions. As these ions migrated into the CEP structure (as a result of the small size of the ions), a discernable current results. Now as the voltage is swept more negatively (e.g., rightwards), the CEP begins to lose the positive charges and is said to be reduced.

To maintain charge neutrality at say about $-0.3$ V, one of two things can occur. The previously incorporated anions can leave the CEP network, or a cation species from the surrounding solution can be incorporated. As the voltage is made more negative, the CEP becomes further reduced (e.g., less net positive charge). At about $-1$ V, cations become incorporated, changing the direction and magnitude of current flow. As the voltage is now made more positive (going towards $-0.5$ V), point A is reached, whereas the CEP is in a reduced state, and begins to become more oxidized once again.

If the voltage sweep were slowly repeated, the current peaks A and B would occur at about the same voltages, but the shape of the CV would probably be changed. The resultant hysteresis would represent fouling and decalibration of the CEP electrode, primarily due to the inability of the polymer to readily de-dope the incorporated charges. Thus, data taken with CEP electrodes at constant potentials are not very reproducible, because targets that incorporate to the CEP tend to remain incorporated, until no further incorporation sites remain. This produces loss of detection sensitivity, and the decalibration and electrode fouling are noted above.

Thus, often after a relatively few minutes of use, the electrode must be replaced or cleansed. It is known to reduce a CEP electrode, e.g., to renew it, by slowly recycling the CEP with an appropriate potential, for example, $-1.5$ VDC for ten minutes. Understandably, having to replace a CEP electrode or expel targets that have become incorporated into the CEP by electrically reducing the electrode is undesirably time consuming, and disruptive of routine analysis.

In addition to having the working electrode undesirably and apparently irreversibly altered by the experiment, the prior art configurations of FIG. 1A and 1B suffer from other deficiencies. Because these configurations maintain either the current I or the voltage V constant during measurement, no selectivity exists that would allow recognition, for example, between analytes. Because all anions (or cations) may attach to the CEP electrode, one can only measure total anions (or total cations).

As such, non-selective prior art CEP electrodes cannot detect chloride only or fluoride only because all anions interact with the CEP. Even if some anion species interacted differently to the CEP, the prior art cannot discern between the species. For example, prior art applications of CEPs cannot discern between voltage or current change resulting from a relatively low concentration of a very effectively interacting anion species, as contrasted with a larger concentration of a less effectively interacting anion species. The gross detection signals for each could appear identical.

It has also been known in the art to use non-CEP electrodes, e.g., inert metal electrodes that are coupled to a source of periodic voltage. These techniques are often referred to as pulsed coulometric detection ("PCD") or pulsed amperometric detection ("PAD"). PCD methods generally require a chemical-working electrode reaction as an absolute prerequisite to detection.

Typically PCD is an indirect method where, for example, an initial chemical adsorption reaction between the working electrode and hydrogen establishes an electrical current. This current is then attenuated by an adsorption reaction between the working electrode and a chemical analyte. In such applications, although the working electrode may be platinum it cannot, for example, be gold since hydrogen atoms will not be adsorbed by gold. Conversely, regardless of the working electrode composition, the pre-measurement phase electrode-chemical adsorption requirement precludes indirect measurements for those chemicals that do not adsorb to the working electrode.

An improved variation on the PCD technique is described in U.S. Pat. No. 4,939,924 (July 1990) to Johnson et al. wherein a periodic step potential waveform is coupled to an inert metal working electrode, and wherein current integration compensates for measurement noise. Johnson et al.'s method, termed PS-PCD for potential stepped-PCD, more directly detects analyte in a flow-through cell containing a working electrode.

In this method, a pulse-step or ramp-like potential waveform is applied to the working electrode, and the analyte is electrochemically detected directly by integrating current over the cyclic portion of the total potential waveform. This permits Johnson et al. to detect organic molecules based upon measurement of the electrical charge resulting directly from their electrochemical oxidations.

FIG. 1D depicts the improved PCD technique disclosed by Johnson et al. As shown therein, a solution 2 containing target analytes 10 is exposed to an inert metal working electrode 24, as well as to a reference electrode 6 and a counter-electrode 8. A voltage waveform generator 28 is coupled between the working electrode 4 and the reference electrode and outputs a repetitive voltage waveform, such as the waveforms shown in FIGS. 1E, 1F and 1G. A current integrator 30 integrates current in the working electrode to provide a detection signal to a recorder or other instrument 32. As shown in FIGS. 1E–1G, the voltage waveform output by generator 28 typically has a repetition rate of perhaps 60 Hz, and a peak-peak maximum excursion of perhaps one or two volts. The waveform has a first potential value E1, whereat the surface of the working electrode exists at an oxide-free state. The waveform potential then increases from E1 to a higher magnitude E1', to allow an oxide to form on the working electrode surface, with concurrent electrocatalytic oxidative reaction of soluble and/or analyte. The waveform potential returns to the first value E1 for a holding time during which the oxide that formed on the working electrode surface is cathodically stripped off. If the potential is held at E1' sufficiently long, no further oxide reduction is required. Otherwise, the potential may then be elevated to a higher magnitude E2, to accomplish a more thorough oxidative cleaning of the electrode surface. If brought to a negative-most potential E3, electrode reactivation by cathodic dissolution of the surface oxide formed at E1 and/or E2 can occur.

In FIG. 1D, the total time of the detection period is the time at potential E1 plus the time at (or enroute to) potential E1'. Current integrator 30 is activated when potential E1 is first presented, and the integrated current output is sampled after E1', at the end of the return to potential E1.

Unfortunately, an inherent limitation in PCD, PAD, and PS-PCD prior art systems is that electro-inactive analytes cannot be detected. Absent the presence of an electrical charge resulting from an associated electrochemical oxidation, such targets go undetected.

In summary, there is a need for a method and apparatus for detecting targets, including electro-inactive analytes, in a stable, reproducible manner that provides selectivity while inhibiting contamination of the working electrode. Preferably such method and device should find application in flow injection analysis, liquid, and ion chromatography, as well as in capillary electrophoresis.

The present invention discloses such methods and apparatus.

SUMMARY OF THE INVENTION

The present invention provides a conductive electroactive polymer ("CEP") working electrode to which is coupled a periodic pulsed or other transient voltage waveform. The voltage waveform apparently causes the CEP to change form, such that one form promotes a detectable interaction with a target analyte, whereupon at least one electrode characteristic is affected in a reversible manner. The reversible nature of the detection enables the CEP electrode to detect a variety of analytes, including anions, cations, organic acids, amines, metal complexing groups, antigens, antibodies, enzymes and other targets of interest. Selective detection occurs in a stable and reproducible manner, without electrode fouling or a hysteresis effect in the detection data. Further, by altering the CEP during fabrication, additional detection selectivity may be provided.

Analytes such as ions and cations are sufficiently small to be incorporated (or "doped") into the CEP backbone when the transient voltage is at a first magnitude, and to be unincorporated (or "dedoped") when the voltage is at a second magnitude. By transitioning the voltage rapidly enough, the doping/dedoping can be reversed, thereby eliminating electrode fouling, decalibration, and data hysteresis. As the target analyte is reversibly incorporated into the CEP network, the resultant charge re-balancing can change the CEP network characteristics, permitting current change to signal detection, for example.

When the target analyte is a biological molecule, the molecular size is too large to permit intimate incorporation into the CEP structure. However, by binding a suitable receptor to the CEP electrode (e.g., an antibody when detecting an antigen), the mating interaction of a large target analyte with its receptor may be detected. The mating interaction does not appear to alter the CEP network per se, but appears to alter conformity of the bound receptor, which may less directly affect characteristics of the CEP network in a measurable manner.

In one aspect, CEP detection selectivity is imparted by controlling the point in time when current is sampled relative to transient voltage waveform coupled to the CEP electrode. In detecting analyte, different currents may be measured as a function of time, depending upon the kinetics of the reversible analyte/electrode interaction.

In another aspect, selectivity may be maintained by the nature of the applied transient potential waveform, which may be pulsed, stepped, ramped, or otherwise varied as a function of time. Detection selectivity may thus be controlled by modifying the applied potential waveform while holding the current sampling point constant.

In yet another aspect, the chemical composition of the CEP is used to affect detection selectivity, with variations in the CEP chemical composition preferably being achieved during polymer synthesis. The nature of the monomer, co-monomers to be polymerized and the supporting electrolyte can result in different conducting polymers, each having unique detection selectivity.

Detection according to the present invention may be used with flow-through electrochemical cells, flow injection analysis, liquid, and ion chromatography, as well as in capillary electrophoresis. Relevant interactions between the CEP and a target can include specific and non-specific adsorption, photometric effects, spectro-electrochemical effects that can cause color change. Measured parameters altered by the CEP state change include Current, resistance, capacitance or mass change. Differential and confirmatory analyses may also be provided by using multiple CEP electrodes coupled to the same or differing transient voltage sources, including the use of CEP electrodes that differ from each other.

Other features and advantages of the invention will appear from the following description in which the preferred embodiments have been set forth in detail, in conjunction with the accompanying drawings.

BRIEF DESCRIPTION OF THE DRAWINGS

FIG. 2A depicts a generic flow injection analysis system providing conductivity and amperometric detection, according to the present invention;

FIGS. 2B and 2C depict voltage generator output waveforms that may be used with the present invention;

DETAILED DESCRIPTION OF THE PREFERRED EMBODIMENTS

Figure 1A:
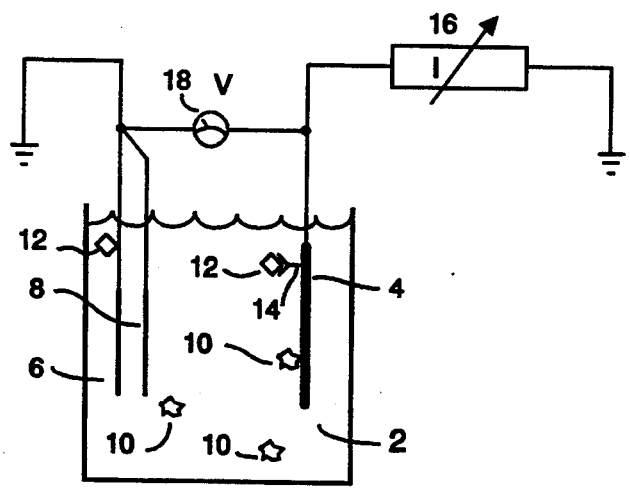
FIG. 1A depicts a generic potentiometric configuration for detection of a target using a CEP to which is coupled a slowly varying current source, according to the prior art.
Figure 1B:
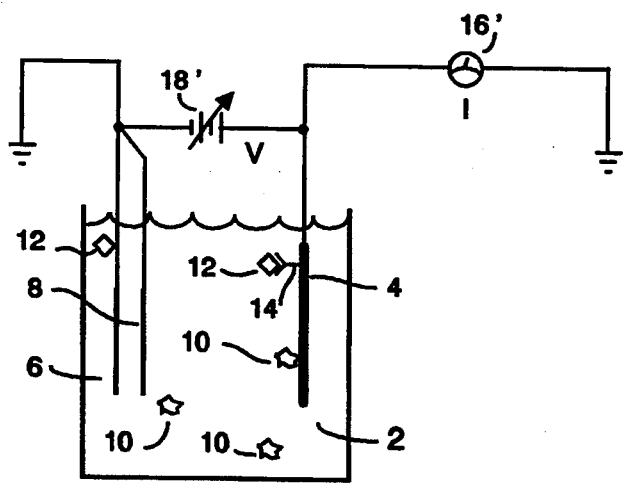
FIG. 1B depicts a generic amperometric configuration for detection of a target using a CEP to which is coupled a slowly varying voltage source, according to the prior art.
Figure 1C:
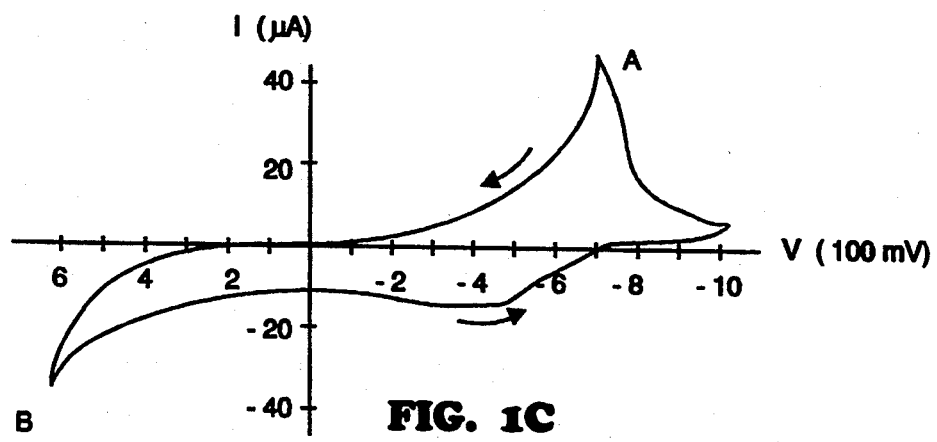
FIG. 1C is a cyclic voltammogram showing the hysteresis in detection data characteristic of non-reversible CEP interactions and CEP fouling using the configuration of FIG. 1A or FIG. 1B, according to the prior art.
Figure 1D:
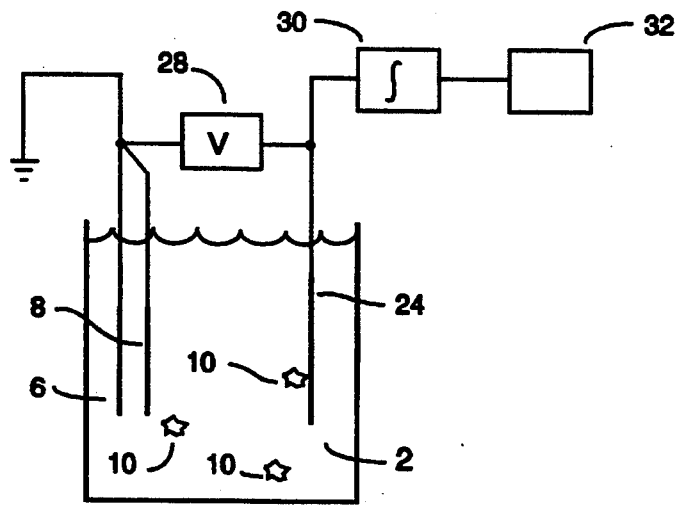
FIG. 1D depicts a generic stepped-potential PCD ("PS-PCD") configuration for detection of an electroactive analyte using a metal working electrode to which is coupled a source of stepped potential, according to the prior art.

As used herein, it is understood that the term "target analyte" (e.g., element 10, FIG. 1A) is whatever analyte the experimenter selected for determination or measurement. With respect to the present invention, target analytes can include (without limitation) organic ions, low molecular weight targets such as organic acids, amines, including heavier weight biological type molecules such as proteins, peptides. Because the present invention may be coupled to an ion chromatographic separator as a detecting mechanism, the target analytes also include all analytes that might be separated using ion chromatography.

Further, as used herein, "immobilized receptors" (e.g., element 14, FIG. 1A) typically are relatively large molecules that are incorporated into the CEP, which molecules have some biological activity or interaction. Such receptors (and their counterparts, e.g., element 12, FIG. 1A) can include antibodies, antigens, enzymes, enzyme substrates. Typically such receptors include receptors that may be the subject of immunoassays, e.g., monoclonal antibody, polyclonal antibody.

As used herein, "oxidation" refers to the form of the polymer, and can set up a favorable environment for doping (e.g., incorporation of a target analyte into the CEP structure), but oxidation per se does not ensure doping.

By way of overview, the present invention may be considered to function using two fundamental mechanisms or models. The first mechanism is associated with detecting small target analytes wherein polymer charge balance seems to play a significant role. The second mechanism is associated with detecting larger analytes, wherein the charge moiety of the polymer backbone (or network) appears not to be intimately affected directly by the desired interaction.

Small target analytes, e,g., anions, cations, under the proper conditions can be brought into or incorporated or doped into the polymer network (or "backbone"), or be unincorporated (or de-doped) therefrom. More specifically, a pulsed or transient voltage source is coupled to the CEP electrode. When the voltage is at one level, the target analyte is incorporated into the polymer, but when the voltage is at a different level, the target analyte may be removed from the polymer. By pulsing or switching between these voltage levels sufficiently rapidly, the analyte incorporation is made reversible, e.g., when the other voltage level occurs the analyte may be unincorporated.

This advantageously allows detection according to the present invention to occur without, for example, fouling the electrodes, or decalibrating the detection system, as occurs in the prior art. This first mechanism appears to rely upon charge balance as a thermodynamic driving force that gets the target analytes into the CEP structure. (By contrast, biological target analytes generally are too large to enter into the CEP network.) As they are incorporated into the polymer network, the incorporated analytes alter the polymer in a manner permitting measurement, for example by monitoring current. As they enter the network, the analytes neutralize the typically positive charge on the polymer, and in the process water molecules are also brought in. As a result, there can be a conformational change and a water content change associated with the polymer.

By contrast, the second mechanism is associated with larger target analytes (e.g., antigens, antibodies), and appears not to rely upon charge balance. These target analytes are too large to enter discretely into or alter the CEP backbone or network. In detecting such targets, a receptor (to which the desired target analyte matingly attracts) is attached to the CEP electrode before the experiment. When the applied voltage causes the CEP to be in one form, as the target analyte interacts with the receptor (e.g., an Ab-Ag interaction), the receptor appears to alter the polymer conformation, and to alter the ability of the polymer as a whole to carry a charge.

In addition to undergoing a conformal change, as the polymer is oxidized (generally due to positive charging), the positively charged sites require negative charge (e.g., an ion) to attain charge balance. The negative ion (e.g., chloride) brings water into the polymer, thus increasing the water content of the CEP. Biological interactions (e.g., Ab-Ag) seem to require conformation in orientation to occur. As the CEP electrode is pulsed, the receptor (and possibly the CEP surface) undergo conformational change. It is this conformational change that appears to allow or not allow interaction with a mating target analyte.

FIG. 2A depicts a generic flow injection analysis system, according to the present invention. As shown therein, a liquid flow stream containing the target to be detected is provided as an output from a pre-detection system 30, for example a flow injection analyzer, a liquid or ion chromatograph, a capillary electrophoresis system, among other systems. Commonly, this stream may pass through a conductivity detector 32 and is presented to an electrochemical flow detection cell 34. (A preferred embodiment of flow detection cell 34 is described in detail with respect to FIG. 6.)

Flow detection cell 34 includes at least one working CEP electrode 36, a reference electrode 38 that typically is silver/silver chloride, calomel and/or pH, and a counter-electrode 40 that typically is an inert metal such as stainless steel or platinum. However, in some applications, counter-electrode 40 may also have a CEP coating that is the same or that differs from the CEP associated with the CEP working electrode 36. Upon passing through flow cell 34, the liquid stream may be discarded, typically into a waste receptacle 42.

Figure 1E:
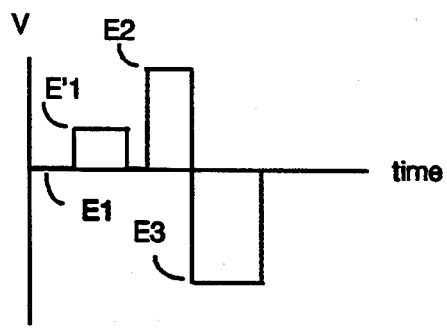
FIGS. 1E-1G represent voltage generator output waveforms that may be used with the prior art configuration of FIG. 1D, as well as with the present invention.
Figure 1F:
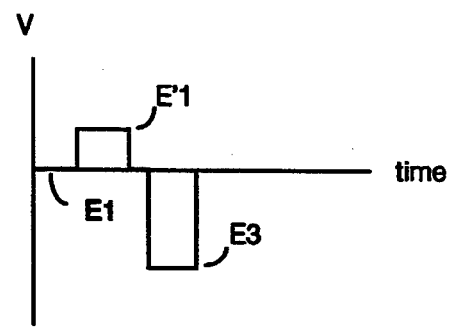
Figure 1G:
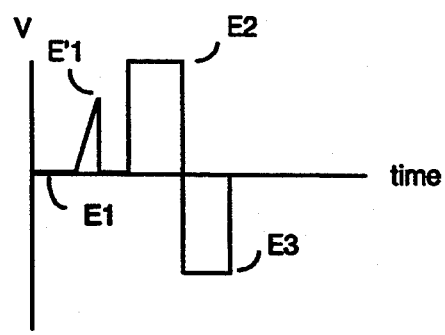

A voltage waveform generator 44 is coupled between the working electrode and the reference electrode. Generator 44 outputs a preferably periodic voltage waveform that may be ramp-like, pulse-like, or a combination thereof, with peak-peak output voltage ranges as large as about 4 V (e.g., +2 V to −2 V) to as small as 50 mV, with a repetition rate of perhaps about 1 Hz to about 60 Hz. Typical waveforms output by generator 44 are shown in FIGS. 2B and 2C, and in fact waveforms shown in FIGS. 1E–1G may also be used.

Typically a high gain, low noise preamplifier 46 is coupled to the CEP working electrode 36, to provide signal amplification, and if desired, additional monitoring devices 48 may also be coupled to the CEP working electrode. Preferably a Faraday cage 50 encloses the flow cell and related components, as shown in FIG. 2A. The output from preamplifier 46 may be coupled to a detector 52, whose output may be displayed, for example with a recorder 54.

The nature of the analytical signal to be measured determines what type of detector 52 is used. For example, to measure the current associated with the CEP electrode, an amperometric detector would be used. However, CEP electrode resistance, capacitance or change in mass may also be used as detection signals.

The configuration of FIG. 2A has some similarity to what is used for pulsed amperometric detection (PAD). However, the present invention uses a CEP working electrode rather than a bare gold or other inert metal electrode. Of course, more than one CEP working electrode 36 may be used within cell 34. The multiple CEP working electrodes need not be identical to each other, and may be coupled to multiple voltage generators 44, not all of which need output an identical waveform. It will be appreciated that using multiple CEP working electrodes, voltage generators, and detectors can provide differential and confirmatory analysis functions.

Applicants' CEP working electrode is a preferably inert metal conductor (e.g., stainless steel, platinum, gold), whose surface is covered with a CEP material. The working electrode may have a range of dimensions, for example, a CEP diameter of about 0.01 mm to about 10 mm, surrounding an innermost inert metal conductor. CEP electrodes with diameters less than about 50 μm are referred to as microelectrodes and can provide better sensitivity and electrochemical control than their macroelectrode-sized counterparts.

The CEP may be applied to the metal conductor to form a working electrode in a variety of ways, known to those skilled in the art. Without limitation, CEP working electrodes may be formed by electro-deposition or electropolymerization using potentiodynamic, potentiostatic, and galvanostatic techniques, or by the evaporation application of a monomer solution in an appropriate solvent.

However, it must be emphasized that detection according to the present invention involves considerably more chemistry that occurs when using prior art techniques, including PCD, PAD and potential-stepped PCD. Applicants believe that in the present detection, upon oxidation and reduction of the CEP working electrode, an ion exchange mechanism occurs. Anions and even cations can become reversibly incorporated into the CEP, during doping and de-doping. In addition, a conformational and/or water content change (hydration change) may occur in the CEP during the oxidation and reduction processes.

The present invention can achieve detection by monitoring changes in the state of the CEP electrode related to the detection event, for example, the reversible binding of a target analyte, (e.g., the interaction between a target antibody or antigen with its immunological counterpart). Such incorporation or interaction events seem to alter the structure of the CEP in a manner allowing at least one characteristic associated with the CEP to be monitored as a detection signal. However, the mechanisms whereby such events reversibly alter the CEP structure to provide a measurement signal have not been proven.

When a potential is coupled to the CEP electrode, e.g. by generator 44, incorporation or interaction events seem to alter the CEP structure such that working electrode current provides a measurement signal. The current seems to result from several phenomena, which are the subject of continuing research.

One current component seems to be a Faradaic current that arises due to the oxidation or the reduction of the polymer as a result of the gross potential applied by generator 44. However, the magnitude of this Faradaic current components depends upon how readily a positive charge occurring on the CEP in an oxidation phase can be satisfied by some anion in the solution surrounding the CEP electrode. For example, relatively mobile anions can readily attach, more of the CEP will be oxidized, and a large current component should result.

However, the same anion also appears to give rise to a related but different current component, apparently due to migration of the anion into the polymer network.

There may also be a current component arising from cation migration in the event a counter-ion in the CEP is not readily expelled therefrom. If such counter-ion remains, as the voltage generator causes the CEP electrode to become reduced, a charge imbalance will arise because the anion still remains incorporated into the CEP network. At this juncture, a cation from the surrounding solution can migrate into the polymer network to satisfy the anionic component in the polymer. By way of example, assume that the CEP working electrode is in a reduced state surrounded by a solution containing sodium chloride. The voltage generator then provides a pulse that: causes oxidation of the CEP working electrode, which becomes positively charged. Chloride can then associate with the polymer to satisfy the positive polymer charge, at which point the CEP is analogous to an anion exchanger.

By way of further example, rather than sodium chloride, substantially larger and less mobile anions may be present, e.g., sodium octane sulfonic or octane sulphonate. To some extent, these anions associate with the CEP during oxidation to satisfy the polymer charge. However, when reducing the CEP working electrode, these anions bind strongly to the positive charge due to their high affinity for the positive portion of the polymer. In this example, either because it is so tightly held or has low mobility, the anion is less likely to be expelled from the polymer. CEP working electrode reduction still occurs, but the anion remains. To maintain charge neutrality, a cation must enter and be incorporated into the polymer network, giving rise to a migration current component.

The present invention advantageously seeks to use the existence of these simultaneous chemistries to modulate the parameter under measurement, current for example. Several working examples wherein data were collected using a CEP electrode according to the present invention will now be described.

EXAMPLE 1

Pulsed Electrochemical Detection of Electro-inactive Ions in Flow Injection Analysis Using Macro-sized CEP Electrodes In the first example, the present invention was used to detect electro-inactive ions in a flow injection analysis, which detection would not be possible using conventional PAD, PCD, or even PS-PCD techniques.

Macro-sized polypyrrole electrodes were prepared by galvanostatically electropolymerizing pyrrole monomer (0.1M) from aqueous solution onto a platinum substrate. The platinum electrode was polished using a cloth and alumina, and was then ultrasonicated before electropolymerization. Counter-ion solutions for polymerization contained sodium salts of 0.5M chloride, acetate, dodecylsulfate, phosphate or carbonate. Based upon published literature, under these conditions 24 mC/cm$^2$ is assumed to yield CEP films of about 0.1 $\mu$m thickness. Solutions were deoxygenated with nitrogen for 10 minutes before electropolymerization. The polypyrrole was deposited for five minutes using 0.85 mA/cm$^2$ current densities.

A flow injection analysis experimental setup as shown in FIG. 2A was used, with voltage generator 44 initially providing a steady DC output potential. Applicants considered the detection of anions including chloride, nitrate, phosphate, carbonate, acetate, and dodecylsulfate (DS). Unless otherwise stated, in all cases the cation employed was sodium.

An appropriate voltage potential must be employed to detect ion exchange processes, and the following data were obtained with the CEP electrode coupled to a constant potential rather than a transient potential waveform. A potential of $-1.00$ VDC was applied for 3 minutes, after which the effect of the anodic (oxidative) potential on the current peak height for nitrate was investigated. (Nitrate was selected because voltammograms for all electrodes were well defined in this media.) Using flow injection analysis, the response obtained increased with increasing anodic potential, but polymer degradation was observed at potentials more positive than $+0.6$ V, with similar trends being obtained for all electrodes independently of the analyte under consideration.

These data suggested that for constant potential analysis, an anodic potential of about $+0.4$ V would give reasonable sensitivity. Further, the working electrode lifetime would be extended, since at a $+0.4$ V potential the polymer would undergo normal ion exchange processes while in its oxidized form.

Figure 3:
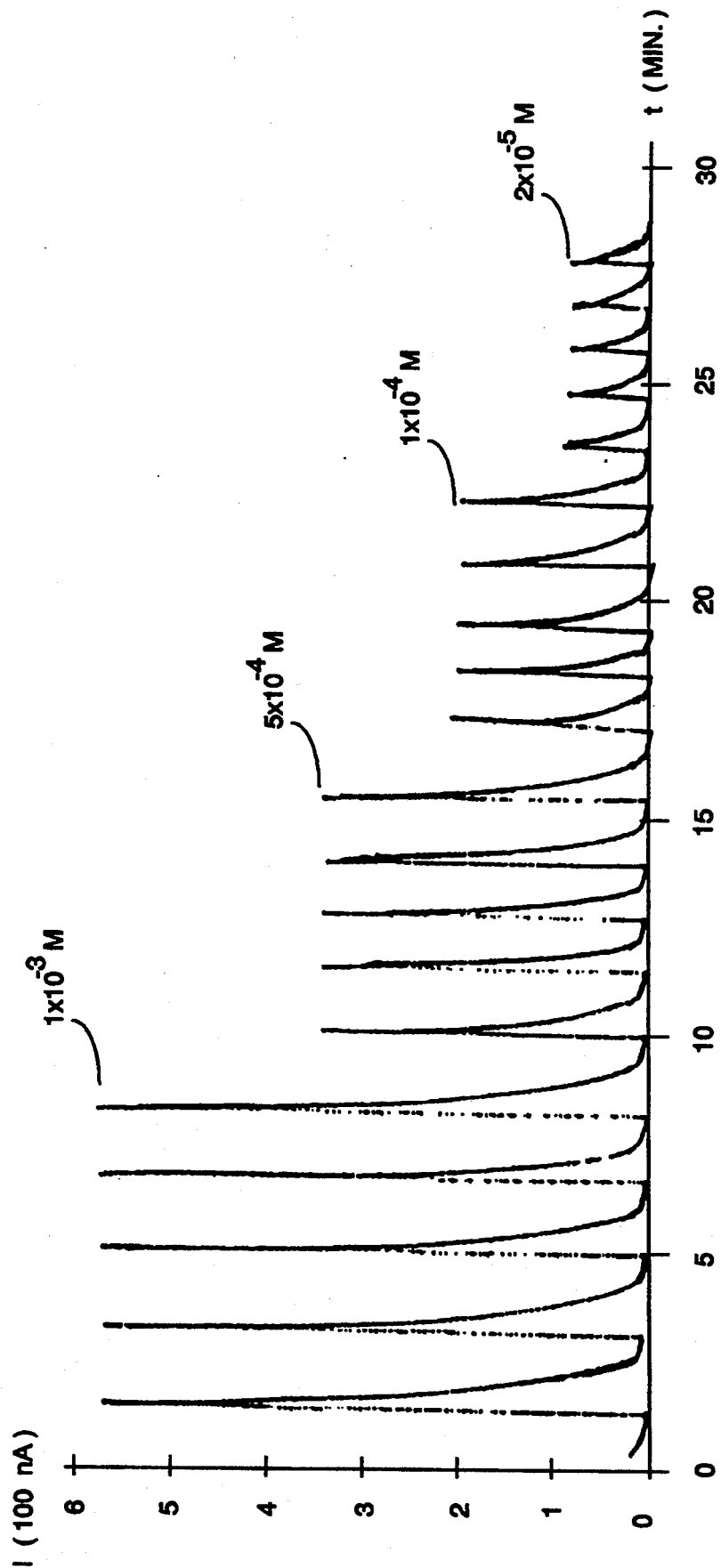
FIG. 3 depicts responses obtained for the configuration of FIG. 2A for injection of different concentrations of $NaNO_3$ solution using a polypyrrole (PP)/$NO_3$ CEP electrode coupled to +0.4 VDC.

FIG. 3 depicts measured current responses obtained for the configuration of FIG. 2A, as a function of nitrate solution concentrations injected into the detection cell 36, using a PP/NO$_3$ electrode coupled to $+0.4$ V, 1M glycine carrier and a 1.0 mL/minute flowrate. As shown, there is a discernable difference in measured current for solution concentrations ranging from $2.10^{-5}$M to $1.10^{-3}$M.

Figure 4B:
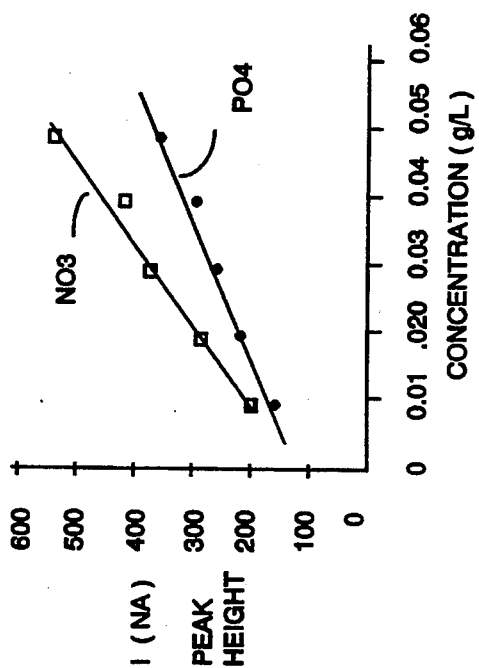
FIGS. 4A-4D depict calibration curves obtained with the configuration of FIG. 2 for selected analytes.
Figure 4D:
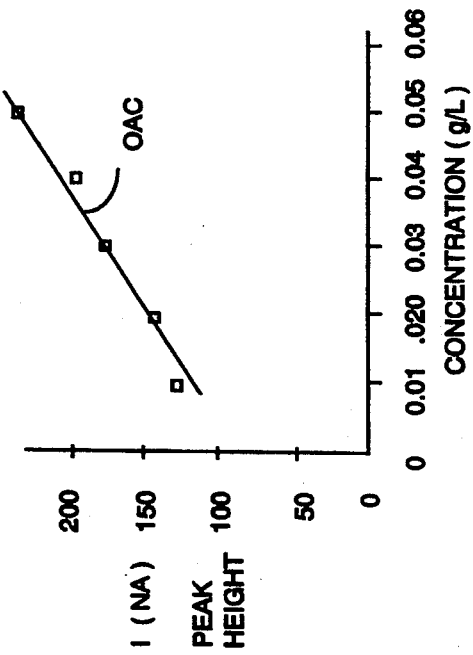
Figure 4A:
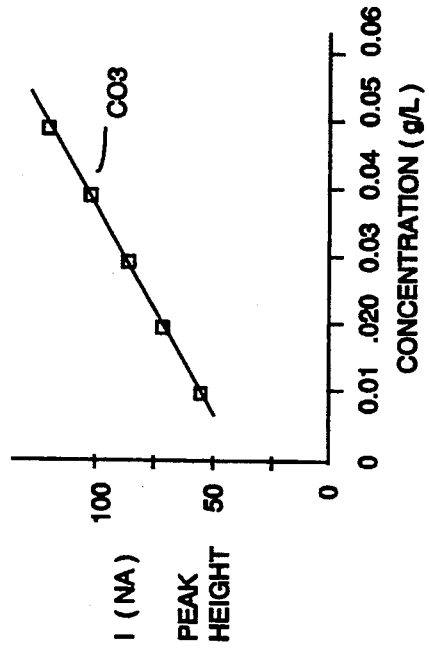
Figure 4C:
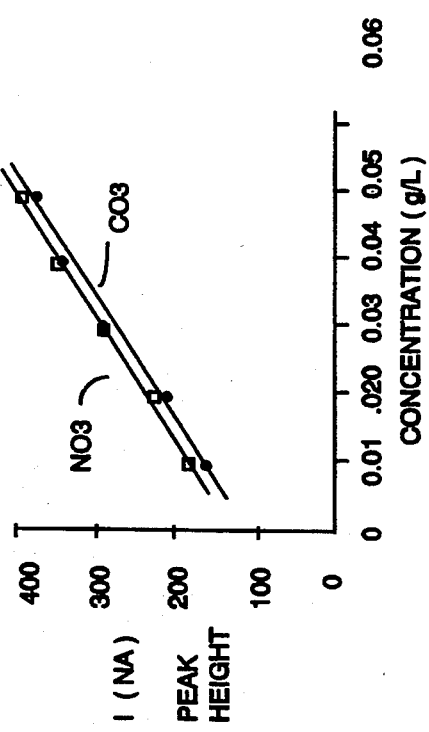

Flow injection analysis calibration curves obtained at higher analyte concentrations for selected species are shown in FIGS. 4A–4D. These data were obtained with the configuration of FIG. 2A, wherein the carrier was 1M glycine, the flow rate was 1.0 mL/minute and the injection volume was 50 $\mu$L. In FIG. 4A, a PP/Cl (PP/chloride) electrode was used, and the analytes were NO$_3$ and CO$_3{}^{2-}$. In FIG. 4B, the electrode was PP/NO$_3$ and the analyte was CO$_{32}$. Data in FIG. 4C was obtained for a PP/PO$_4{}^{3-}$ electrode, and CH$_3$COO analyte. FIG. 4D was obtained using a PP/DS electrode, and NO$_3$ and PO$_4{}^{3-}$ analytes.

With further reference to FIGS. 4A–4D, at lower concentrations the calibration curves obtained were mostly nonlinear, presumably due to the signal generation mechanism being distorted by the low ionic strength of the media. For this reason, detection limits were limited to the 10$^{-5}$M region.

Table I, below, shows analyte ion sensitivities taken from the linear portion of the above-described calibration curves.

TABLE I

| Electrode | Sensitivity (nA/mMol) | | | | | |
|---|---|---|---|---|---|---|
|  | NO$_3{}^-$ | PO$_4{}^{3-}$ | Co$_3{}^{2-}$ | CH$_3$COO$^-$ | Cl$^-$ | DS$^-$ |
| PP/Cl | 4800 | 1000 | 5200 | 0.0 | 15000 | 0.0 |
|  | (9840) | (1248) | (2700) | (560) | (45000) | (480) |
| PP/DS | 8300 | 3750 | 200 | 760 | 115 | 100 |
|  | (8460) | (4000) | (2680) | (880) | (NA) | (NA) |
| PP/PO$_4$ | 500 | 300 | 440 | 2750 | 120 | 100 |
|  | (2040) | (4860) | (2300) | (1000) | (1400) | (260) |
| PP/NO$_3$ | 200 | 360 | 1630 | 300 | 140 | 260 |
|  | (1500) | (2441) | (1600) | (1680) | (900) | (1080) |

In Table I, non-bracketed data represent sensitivities obtained using a constant $+0.4$ VDC potential without undoping, whereas bracketed data denote sensitivities obtained using 60 ms pulses ranging from $+0.4$ V to $-1.0$ V. Hence, as shown in Table I, pulsing improved sensitivity for all ions investigated.

Applicants then used surfactant-containing eluent, namely sodium dodecylsulfate (SDS) as a carrier, with a view to altering electrode sensitivity. Sensitivities were then taken from the linear portion of the curve and are shown in Table II.

TABLE II

| Electrode | Sensitivity (nA/mMol) | | | | | |
|---|---|---|---|---|---|---|
|  | NO$_3{}_-$ | PO$_4{}^{3-}$ | Co$_3{}^{2-}$ | CH$_3$COO$^-$ | Cl$^-$ | DS$^-$ |
| PP/Cl | 8400 | 3040 | 1980 | 100 | 21000 | 112 |
|  | (17710) | (14800) | (4800) | (1586) | (5400) | (680) |
| PP/DS | 7252 | 850 | 660 | 1460 | 850 | 140 |

TABLE II-continued

| Elec-trode | Sensitivity (nA/mMol) | | | | | |
|---|---|---|---|---|---|---|
| | $NO_3^-$ | $PO_4^{3-}$ | $Co_3^{2-}$ | $CH_3COO^-$ | $Cl^-$ | $DS^-$ |
| | (18450) | (1040) | (1285) | (13500) | (1680) | (580) |

In Table II, non-bracketed data represent sensitivities obtained using a constant +0.40 VDC potential without undoping, whereas bracketed data denote sensitivities obtained using 60 ms pulses ranging from +0.4 V to −1.0 V, and 0.1M DS as a carrier.

As noted, which carrier is employed influences the attainable selectivity series, especially when considering selectivity factor changes such as sensitivity ratios. With polypyrrole chloride (PP/Cl) in glycine, nitrate/phosphate demonstrates a selectivity factor of 6.8, while using a SDS carrier results in a selectivity factor of 2.5. However, using SDS, the nitrate/acetate ratio is 8.4, while using glycine the ratio is only 1.3. Similarly, for a polypyrrole dodecylsulfate (PP/DS) working electrode, the nitrate/phosphate selectivity factor is only 1.2 in glycine, but 9.2 in a SDS carrier.

This carrier dependence appears to support applicants' hypothesis that ion exchange between the analyte and the CEP contributes to the signal observed. This appears to follow because carrier ions compete for available sites and alter the selectivity. Furthermore, in this carrier conductivity, differences are less marked when the analyte is injected. For example, the specific conductance of 0.1M sodium dodecylsulfate is 5.78 mS, while for 0.01M sodium nitrate the specific conductance is 4.23 mS. The shape of the calibration curves obtained was similar to those obtained using glycine as the eluent, with detection limits restricted to the $10^{-5}$M range.

Applicants believe that the use of a pulsed potential waveform coupled to a CEP working electrode amplifies the detection signal because, in the presence of the analyte, the polymer is continually oxidized and reduced (with attendant anion or cation exchange being encouraged). Even when using a glycine media, the present invention resulted in an increase in detection sensitivity when voltage pulses were coupled to a CEP working electrode. Note, for example, in Tables I and II the sensitivities obtained for glycine and SDS carriers, respectively.

Of particular interest is the changes in relative sensitivities and, hence, selectivity factors attainable. Applicants presume this is because application of pulsed potentials to the CEP working electrode should enable cation (or anion) incorporation/expulsion to play a more predominant role in the signal generation process. For example, the cation may be incorporated into the CEP at negative potentials, but then be expelled from the CEP at positive potentials.

As such, the incorporation/expulsion process associated with the present invention as the voltage coupled to the CEP electrode is transitioned advantageously appears to be reversible in nature. This, of course, is in contrast to what is experienced in the prior art, where electrode fouling, decreasing sensitivity, decalibration and hysteresis are commonplace. Data in Table II suggest that using pulsed potentials with an SDS carrier generally has a more pronounced effect on sensitivity. Further, changes in selectivity could be induced using pulsed potentials coupled to a CEP working electrode in an SDS carrier.

EXAMPLE 2

Pulsed Electrochemical Detection of Electro-inactive Ions in Flow Injection Analysis Using Micro-sized CEP Electrodes As above noted, a unique signal generation mechanism appears to exist with CEPs such as polypyrrole. This mechanism seems to generate signals due to oxidation/reduction of the polymer in the presence of the analyte of interest and an appropriate carrier whose ions are not readily incorporated into the polymer. Oxidation of the polymer then depends upon the presence of more easily incorporated ions (analytes), and the degree of oxidation/reduction depends on the concentration of these species. However, a quandary arises in that the use of carriers with anions that are not readily incorporated will lead to the use of carriers with lower conductivity. In a prior art electrochemical cell, increased ohmic (i.R) drop would result, accompanied by a loss of control over the applied potential and hence over the detection mechanism.

In the present invention, the use of microelectrodes (e.g., electrodes having a transverse dimension less than 50 μm) is accompanied by a smaller detection current, and hence a smaller ohmic i.R drop in low conductivity carriers. Thus, CEP microelectrodes coupled to a source of pulsating voltage (e.g., voltage generator 44) can appreciably reduce ohmic drop. This in turn, minimizes distortion in achieving good potentiostatic control. Further, CEP microelectrode are associated with lower capacitance values, which can advantageously improve signal-to-noise ratios.

Polypyrrole electrodes were prepared by galvanostatic polymerization of the pyrrole monomer (0.5M) from an aqueous solution onto a platinum electrode with diameters ranging from 10 μm to 50 μm. Counterion solutions for the polymerization contained 1M sodium chloride, 1M trisodium phosphate, and 0.1M sodium dodecylsulfate.

Current densities of 2 mA/cm² were used and the polypyrrole was deposited for 10 minutes. Cyclic voltammograms (CV) recorded after the growth of PP/Cl, PP/DS, or PP/PO₄ were similar to those reported previously for macroelectrodes. Well defined oxidation/reduction responses were observed, wherein voltage magnitudes and resultant current magnitudes corresponding to the responses depended upon the nature of the supporting electrolyte. In each case, the current magnitudes of the microelectrodes were lower than current provided from macroelectrodes, the current being markedly lower with PP/PO₄.

Figure 5A:
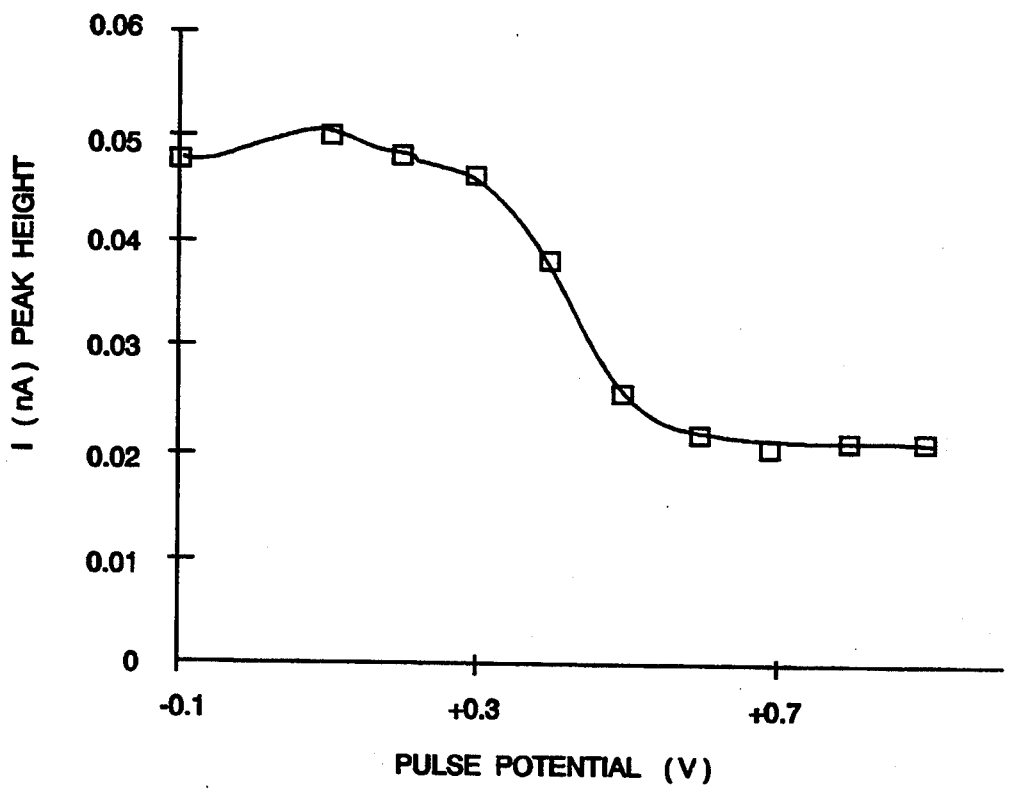
FIGS. 5A and 5B depict hydrodynamic voltammograms for CEP microelectrodes using a glycine carrier.
Figure 5B:
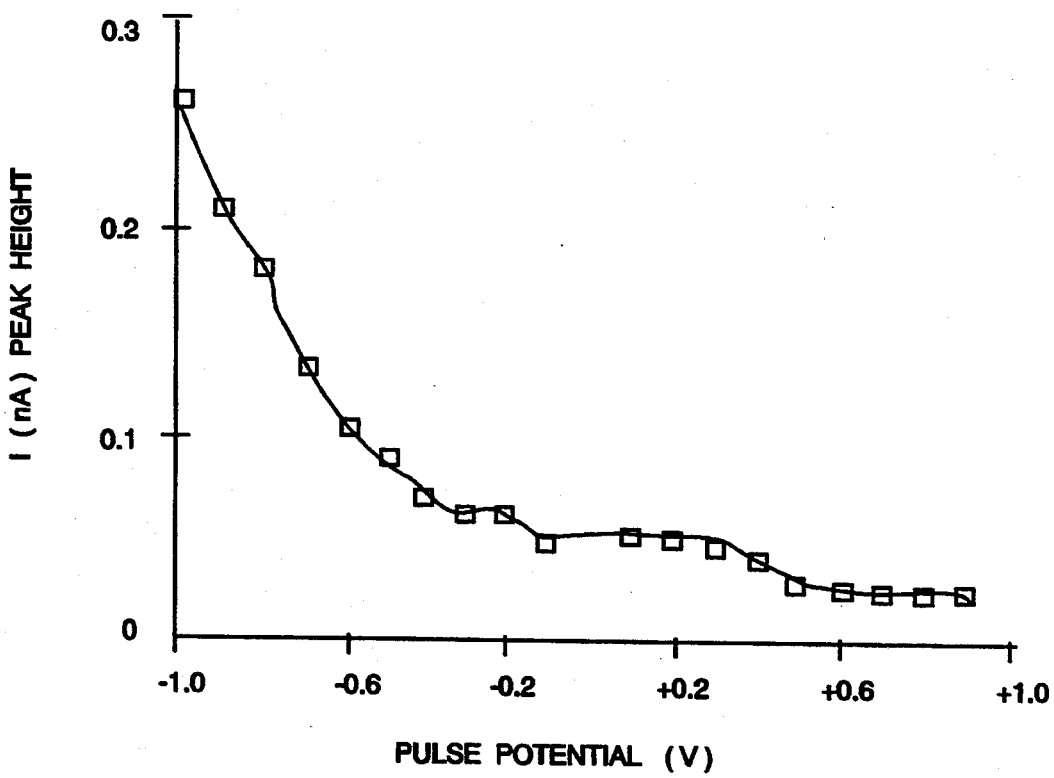

With reference to FIGS. 5A and 5B, cyclic voltammograms were also obtained in glycine for various anions, which CVs exhibited well defined oxidation and reduction responses, provided that the polymer was initially cycled in chloride media. Pulsed hydrodynamic voltammograms ("PHD") were recorded in glycine media, wherein the initial potential (Ei) was held constant at about 0.4 V, and wherein the final potential (Ef) was varied. FIGS. 5A and 5B show such data for NaNO₃ analyte, 5.10⁻²M, with a 1 mL/min flow rate, where the x-axis is Ef, and the y-axis is detected current. In the experiment, ti=60 ms, tf=60 ms, with current sampled at the end of ti (e.g., 60 ms sampling point), with a 350 ms detector response time. These data demonstrate how pulsing to a more negative potential increases sensitivity, apparently due to the reversible doping/de-doping of the polymer.

Signal intensity increased as Ef increased to 0.2 V. Between 0.2 and −0.6 V the signal intensity leveled off but then increased again at more negative potentials, presumably due to cation incorporation. It will be appreciated that the present invention provides efficient pulsed electrochemical control using a potential range that is readily achieved using micro-sized CEP electrodes. This permits anions and cations to be incorporated into the polymer, thus providing detection capability for cations or anions, using the present invention.

Figure 6:
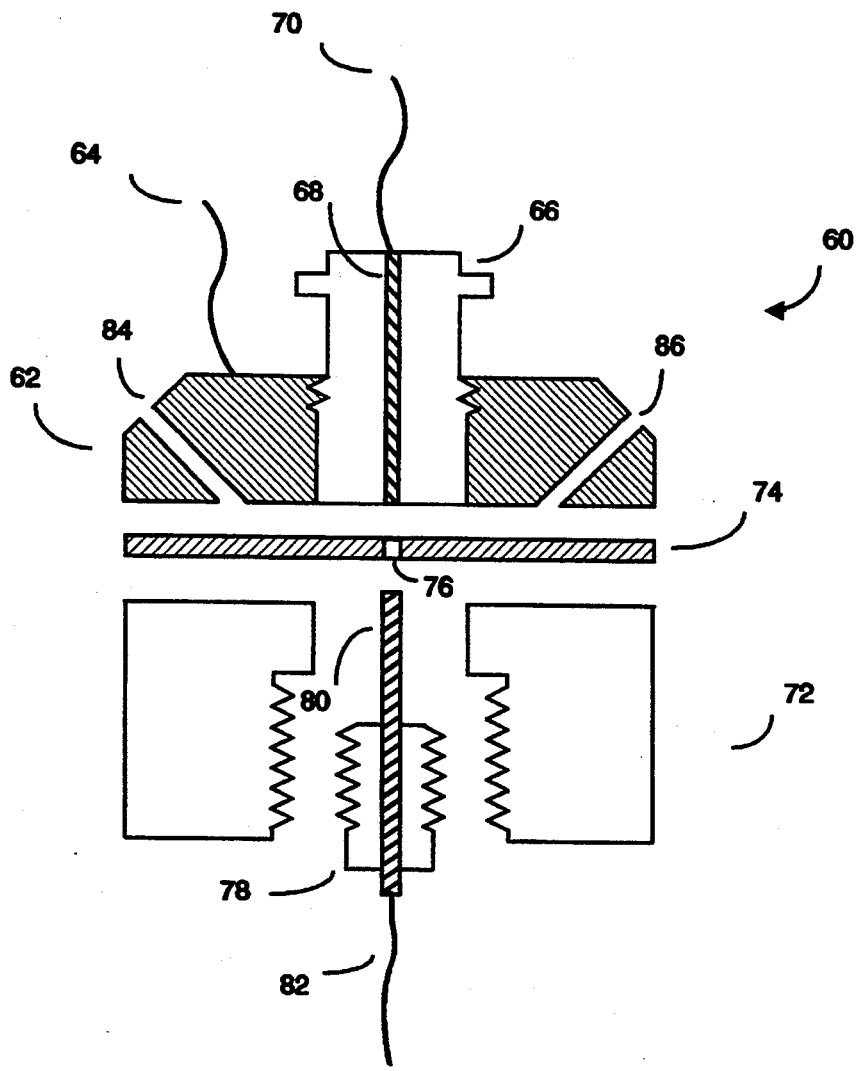
FIG. 6 depicts a microelectrode detection cell, according to the present invention.

FIG. 6 depicts a modified detector cell 60 used to gather micro-sized CEP electrode data, using the flow injection analysis system depicted in FIG. 2A, wherein glycine or water was used as a carrier solution. As such, detector cell 60 is one embodiment of cell 34 as depicted in FIG. 2A.

With reference to FIG. 6, upper portion 62 of the detector cell body itself serves as a counter-electrode (e.g., electrode 40 in FIG. 2A), electrical contact to which is made by wire 64. A retainer 66 holds a reference electrode (e.g., electrode 38 in FIG. 2A), electrical contact to which is made by wire 68. As shown, upper region 62 defines a fluid inlet port 84 and a fluid outlet port 86 through which the solution under examination passes. In the embodiment of FIG. 6A, cell portion 62 was a Dionex thin layer electrochemical cell, model number 37752, available from Dionex Corporation, Sunnyvale, Calif.

Detector cell 60 further includes a lower portion 72, which was fabricated from a 3.7 cm × 2.3 cm × 1.2 cm Teflon TM block containing 25% glass. A spacer 74, fabricated from approximately 0.178 mm thick Teflon TM material, is positioned intermediate portions 62 and 72 and defines a flow channel 76 approximately 0.5 mm wide. A 0.6 cm diameter hole was drilled in the center of the lower portion to accommodate a retainer 78 that holds a platinum wire core CEP working electrode 80 (e.g., electrode 36 in FIG. 2A). Electrical contact to CEP electrode 80 is made via a wire 82.

This configuration of FIG. 6 provides a screw fit for the electrode retainers, thus facilitating removal and replacement of the electrodes. The detector cell configuration shown is readily adaptable to fabrication with other working electrode materials, for example glassy carbon, gold, or carbon paste.

Using the configuration of FIG. 2A, with measurements carried out within the Faraday cage shown, pulsed electrochemical detection of sodium salts of nitrate, chloride, carbonate, phosphate, acetate, and dodecylsulfate was undertaken. Voltage generator 44 provided pulses ranging from +0.4 V to −1.0 V, with current sampled at the end of the positive pulse. A PP/Cl electrode was used with an eluent (carrier) flow rate of 1 mL/minute. For all ions, well defined responses were observed, and detection limits for which are summarized in Table III. In Table III, Ei was +0.4 VDC for ti=60 ms, and Ef=−1.0 VDC for tf=60 ms, with current samples being taken at the end of the Ei pulse.

TABLE III

| Analyte | Macro (ppm) Glycine Carrier | Micro (ppb) Glycine Carrier | Micro (ppb) Water Carrier |
|---|---|---|---|
| $NO_3^-$ | 3.0 | 0.30 | 310 |
| $Cl^-$ | 1.2 | 0.01 | 1.8 |

TABLE III-continued

| Analyte | Macro (ppm) Glycine Carrier | Micro (ppb) Glycine Carrier | Micro (ppb) Water Carrier |
|---|---|---|---|
| $CH_3COO^-$ | 3.0 | 0.03 | 3.0 |
| $CO_3^{2-}$ | 6.0 | 0.60 | 3.0 |
| $PO_4^{3-}$ | 5 | 0.05 | 5.0 |
| $DS^-$ | 5 | 0.95 | 5.0 |

Figure 7A:
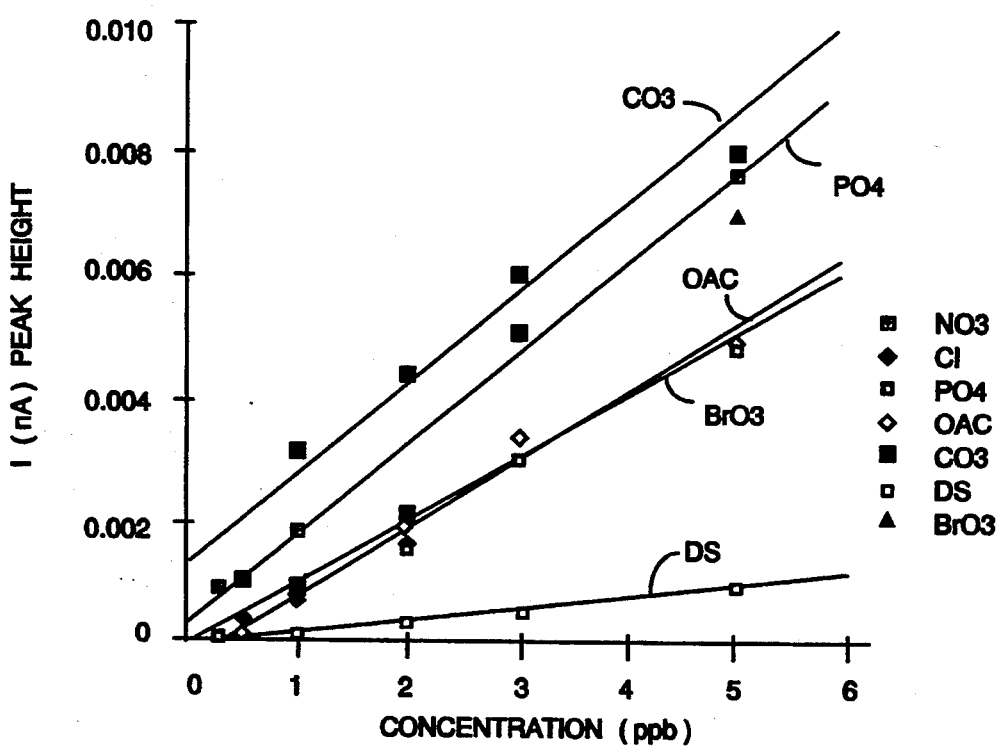
FIGS. 7A and 7B are calibration curves for microelectrodes in glycine eluent and in distilled water eluent, respectively, according to the present invention.
Figure 7B:
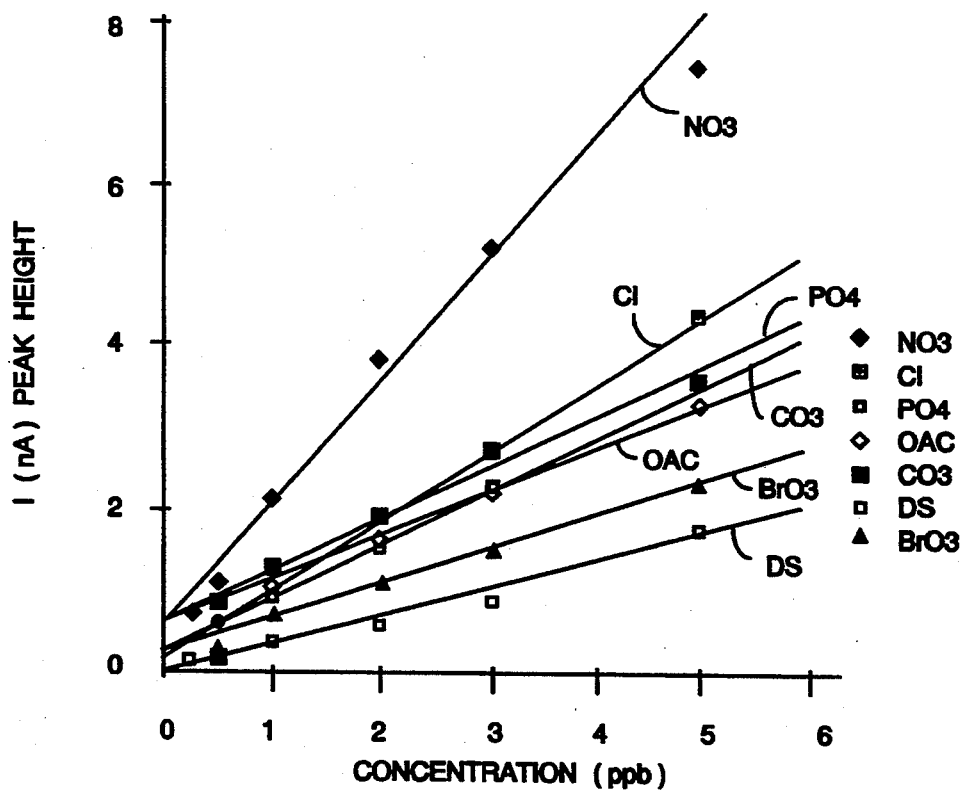

With regard to the data summarized in Table III, responses were linear over the range under investigation, e.g., from the detection limit to $1.10^{-2}$M salt. Calibration curves are shown in FIG. 7A for anions using PP/PO$_4$ microelectrodes and glycine eluent, and in FIG. 7B for PPCl microelectrodes using distilled water as eluent. Table IV summarizes sensitivities (in nA/nMol) obtained from these calibration curves using microelectrodes and glycine as a carrier. Data in FIGS. 7A and 7B were obtained at a flow rate of 1.0 mL/minute, Ei=+0.4 V, Ef=−1.0 V, ti=tf=60 ms.

TABLE IV

| Electrode | $NO_3^-$ | $PO_4^{3-}$ | $CO_3^{2-}$ | $CH_3COO^-$ | $Cl^-$ | $DS^-$ |
|---|---|---|---|---|---|---|
| PP/CL | 233 | 3310 | 336 | 1208 | 344 | 169 |
|  | (9840) | (1248) | (2700) | (560) | (45000) | (480) |
| PP/DS | 48 | 14 | 93 | 55 | 40 | 8.4 |
|  | (8460) | (4000) | (2680) | (880) | (ND) | (ND) |
| PP/PO4 | 1 | 0.90 | 1.3 | 1.0 | 0.9 | 0.9 |
|  | (2040) | (4860) | (2300) | (1000) | (1400) | (2,60) |

In Table IV, bracketed values represent sensitivities obtained using macroelectrodes with pulse electrochemical detection, ND refers to "not detected", and other experimental conditions are as listed above for Table III.

Figure 8:
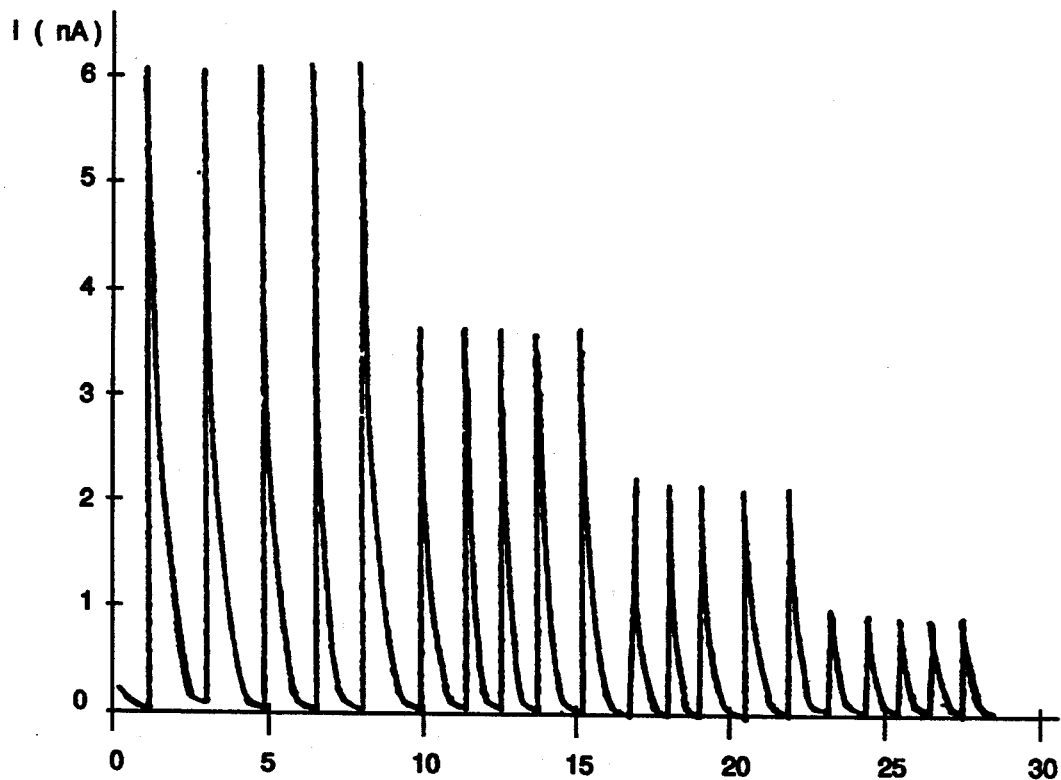
FIG. 8 depicts a series of flow injection analysis system responses, according to the present invention.

FIG. 8 depicts a series of flow injection analysis system responses made with the above configuration, wherein peak current is plotted as a function of time for different sodium nitrate concentrations.

EXAMPLE 3

Figure 9:
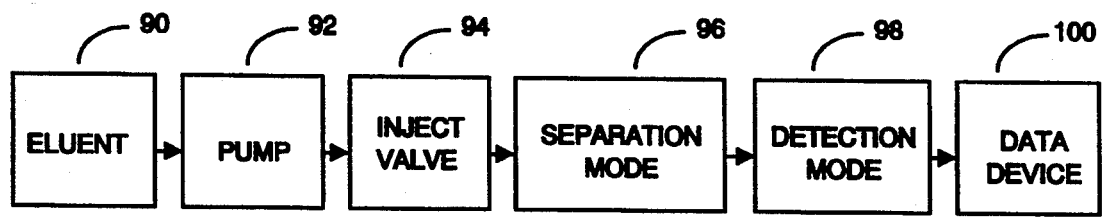
FIG. 9 is a system schematic of an ion chromatography system using suppression, according to the present invention.

Pulsed Electrochemical Detection of Electro-inactive Ions in Ion Chromatography Analysis Using CEP Electrodes and Suppressor In this example, a conventional ion chromatography system using a suppressor device was provided with 3-mm platinum substrate PP/Cl CEP electrodes (whose fabrication is as previously described) and pulsed electrochemical detection. FIG. 9 shows a schematic of this system, wherein eluant 90 is passed by a pump system 92 to an inject valve 94. A separation mode mechanism 96 and a detection mode mechanism 98 are provided, followed by a data service 100. A comparison between applicants' pulsed electrochemical detector with a CEP electrode, and a conventional suppressed conductivity detection may be made by providing a conductivity cell downstream from an electrochemical cell, associated with detection mechanism 98.

Figure 10A:
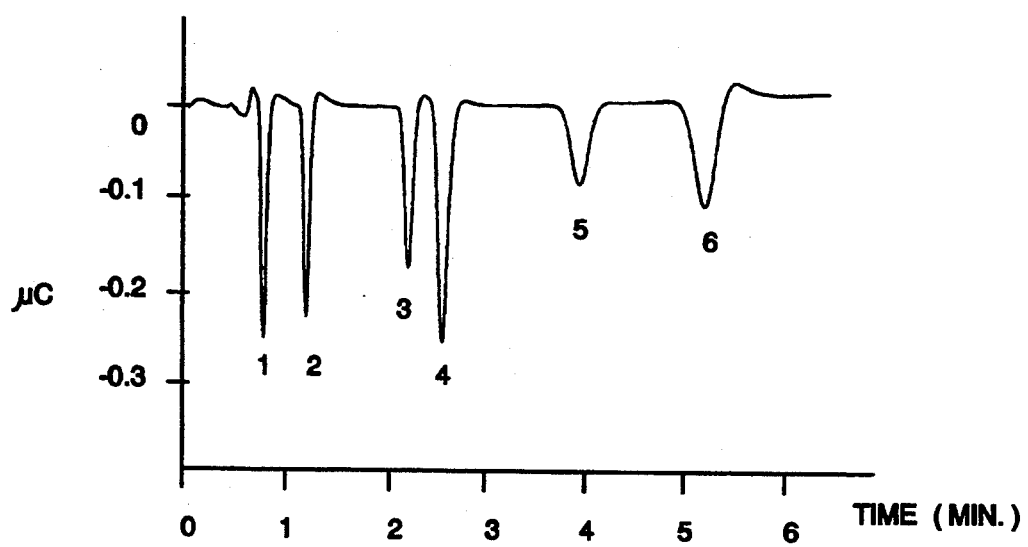
FIGS. 10A and 10B are chromatograms obtained using the present invention.

In FIG. 10A, applicants applied a voltage waveform that was 0 V for about 60 ms, then +0.5 V for 60 ms, then −1.5 V for 60 ms, then back to 0 V for 60 ms, and so on. The current sampling period used for the data in FIG. 10A was 70–160 ms, and for FIG. 10B, the current sampling period was 80–160 ms.

Figure 10B:
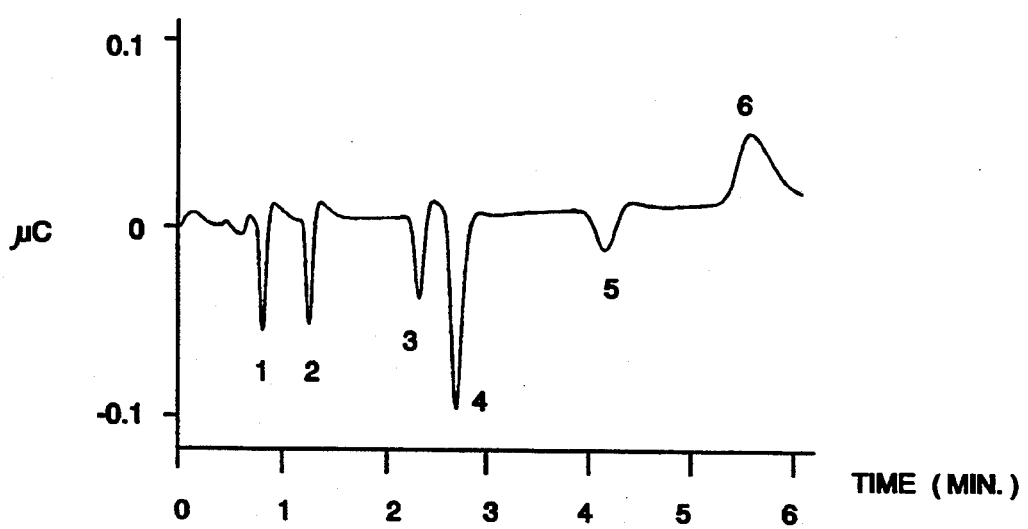
Figure 10C:
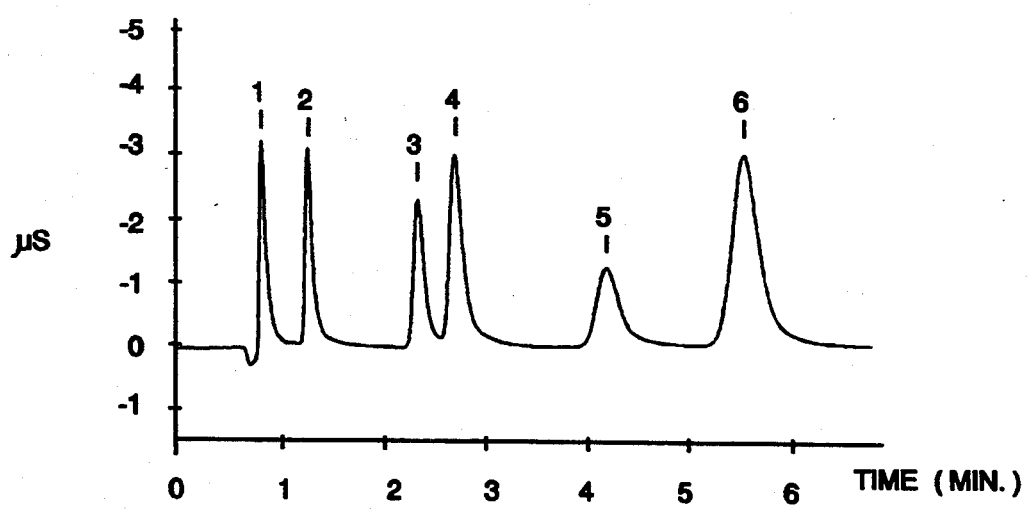
FIG. 10C depicts conductivity detection data obtained using the present invention.

A sodium carbonate and sodium carrier was used in the separation. After passing through the suppressor, the carrier is converted to carbonic acid having low conductivity carrier (16 μS/cm). In FIGS. 10A–10C, described below, the numerals 1 through 6 designate, respectively, $F^-$, $Cl^-$, $Br^-$, $NO_3^-$, $PO_4^{3-}$, and $SO_4^{2-}$.

FIG. 10C shows a typical chromatogram obtained from this system, wherein the column is IonPac AS-4ASC, the carrier is 1.8 mM $Na_2CO_3$, 1.7 mM $NaHCO_3$ with a flow rate of 2.0 mL/min and an injection volume of 20 μL. The suppressor was an AMMS II, available from Dionex Corporation, Sunnyvale, Calif. using 0.012M $H_2SO_4$M H122SO4 regenerant and a conductivity detector (CDM II).

Pulsed electrochemical detection was used to obtain the data shown in FIGS. 10A and 10B, and the pulse sequence and current sampling point appeared to have a very significant effect upon the detector response. For example, changing the current sampling point by only 10 ms inverted the sulfate peaks. This phenomenon indicates the selectivity of this detection technique. See, for example, FIG. 10B, wherein data were taken using the same configuration as in FIG. 10A. Note also the differences in the relative peak height for nitrate compared to the conductivity detection chromatogram (see FIG. 10C, which shows conductivity detection data). Detections limits for most analytes are in the low ppb range, which is comparable to conductivity detection. Data linearity was typical for an ion chromatography system, namely about three orders of magnitude.

Figure 11:
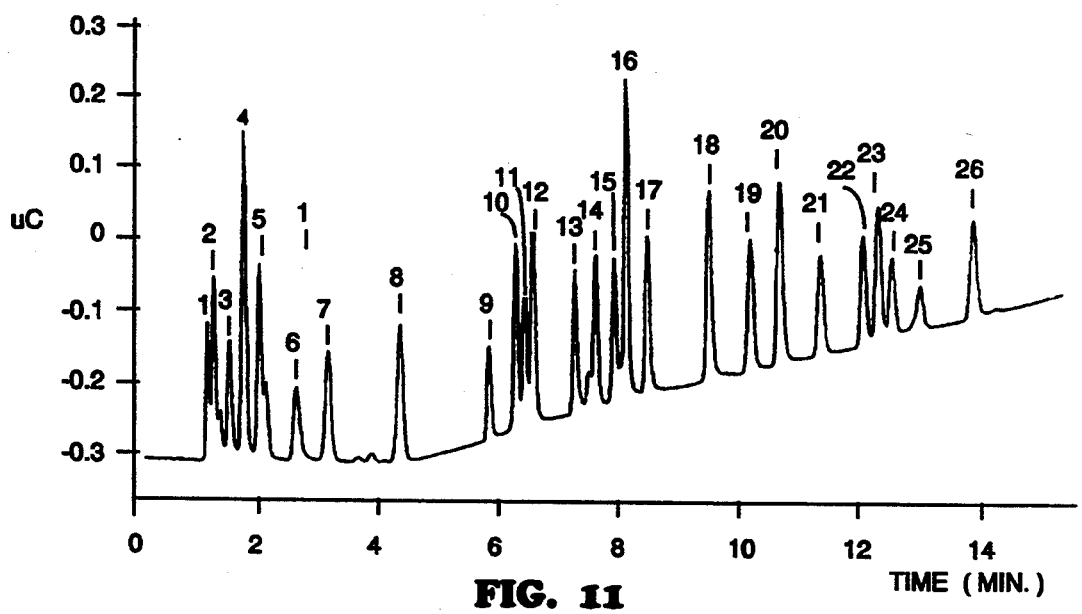
FIG. 11 depicts gradient separation of inorganic and organic anions, with detection according to the present invention.

To test CEP electrodes in a very low conductivity carrier, applicants performed a gradient separation of anions using a sodium hydroxide carrier. In this case, sodium hydroxide was converted to water in the suppressor, the background conductivity was 1–4 μS, and the anions were converted to the acid form. FIG. 11 shows a gradient separation of inorganic and organic anions detected using the detection conditions described with respect to FIG. 10A. The numerals 1–16 shown in FIG. 11 are peak identification numbers. This example demonstrates that CEP electrodes combined with pulsed electrochemical detection can detect a broad range of ions.

EXAMPLE 4

Pulsed Electrochemical Detection of Proteins Using Antibody Containing CEPs

The following embodiment did not involve CEP doping-dedoping, but nonetheless demonstrates the advantages of pulsed electrochemical detection with CEPs for other determinations. This embodiment employs antibodies (Ab) to provide a degree of selectivity previously unattainable in electrochemical sensing.

The inherent molecular recognition capabilities of an antibody (Ab) for the corresponding antigen (Ag) are extremely useful in the present invention. As noted, the prior art has found it difficult to generate a useful, reproducible signal in response to the antibody-antigen interaction, or to permit reuse of a CEP working electrode following an Ab-Ag interaction.

In the embodiment of the present invention under discussion, a desired Ab was bound to the CEP working electrode surface. The working electrode could then be used in a flow injection analysis system, coupled to a source of pulsed voltage such as generator 44 in FIG. 2A.

Polypyrrole anti-Human Serum Albumin (AHSA) was used as a test case. Applicants prepared polypyrrole/AHSA working electrodes by galvanostatically electropolymerizing pyrrole monomer (0.5M) from an aqueous solution containing 100 ppm AHSA solution onto a platinum substrate using a current density of 0.5 mA/cm². Cyclic voltammetry confirmed that normal polymer oxidation/reduction processes occurred. Similar to what had been previously in the art, no change in cyclic voltammetry occurred when the antibody-containing CEP electrode was exposed to HSA.

A flow injection analysis system was used to test the PP/AHSA in a flowing stream. The system was first tested with a constant potential of +0.6 VDC. With this DC potential, analytical responses could be obtained for injections of HSA, but with poor sensitivity and a detection limit of only 25 ppm. Further, the responses produced suffered because tailing peaks were obtained, presumably due to the irreversible nature of the Ab-Ag interaction with a constant applied potential.

Figure 12A:
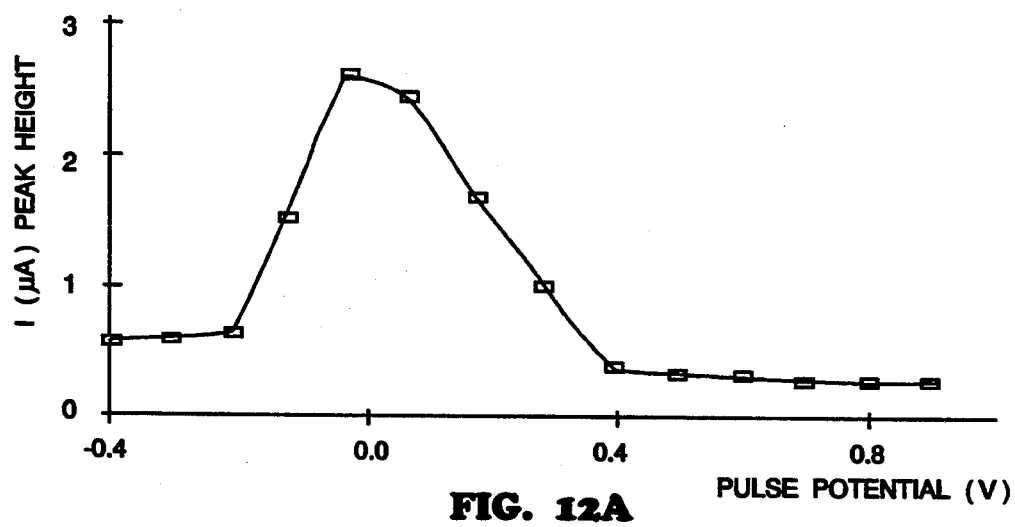
FIG. 12A depicts pulsed potential hydrodynamic voltammogramic Human Serum Albumin (HSA) detection as a function of pulse potential, according to the present invention.

Applicants next investigated the use of a pulsed electrochemical waveform to generate an analytical signal using the PP/AHSA. A pulsed potential hydrodynamic voltammogram was obtained using symmetric 120 ms wide pulses. An initial potential (E1) was maintained at +0.4 VDC, a range whereat Ab-Ag interactions are encouraged. The E2 magnitude was varied between −0.4 V and +0.90 V (see FIG. 12A), with current sampling always occurring at the end of E2.

Pulsing to more positive potentials produced a small signal that did not increase with the potential. However, as the potential was pulsed negative to 0.0 VDC, the signal increased in magnitude. However, but further decreases in the negative potential limit decreased the response. In short, the use of pulsed potentials markedly enhanced the magnitude of the responses obtained. Applicants believe this amplification may be due to increased capacitive currents obtained upon pulsing, and also because pulsing presumably induces multiple Ab-Ag interactions.

Figure 12B:
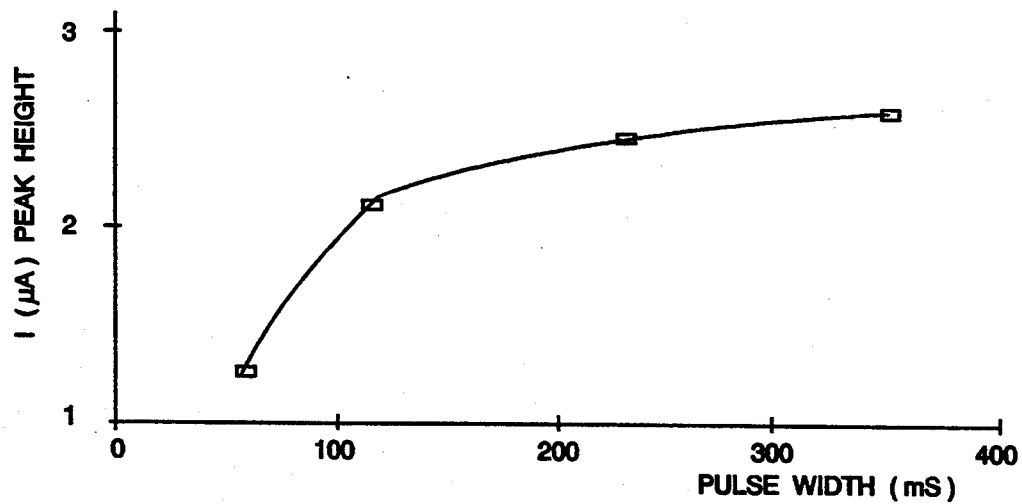
FIG. 12B depicts pulsed potential hydrodynamic voltammogramic HSA detection as a function of pulse width, according to the present invention.

Using these initial and final potential conditions, the effect of pulse width on the response obtained was considered (see FIG. 12B, wherein Ei=0.4 V and Ef=−1.0 V). Applicants found sensitivity increased markedly as pulse width was increased from 60 ms to 120 ms, but increased only marginally with further increases. The variation in sensitivity from 60 ms to 120 ms pulse widths highlights the role played by the kinetics of the Ab-Ag interaction in signal generation.

Figure 13A:
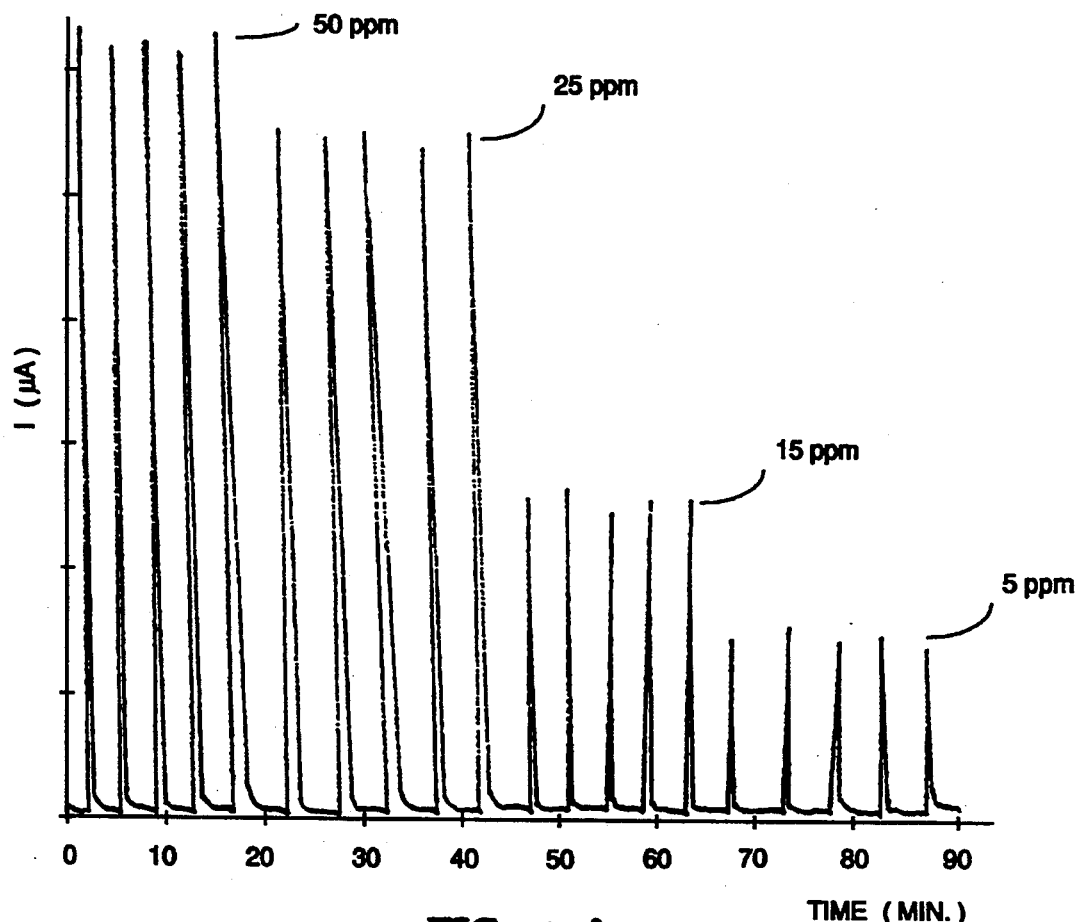
FIG. 13A depicts flow injection analysis response for HSA according to the present invention.
Figure 13B:
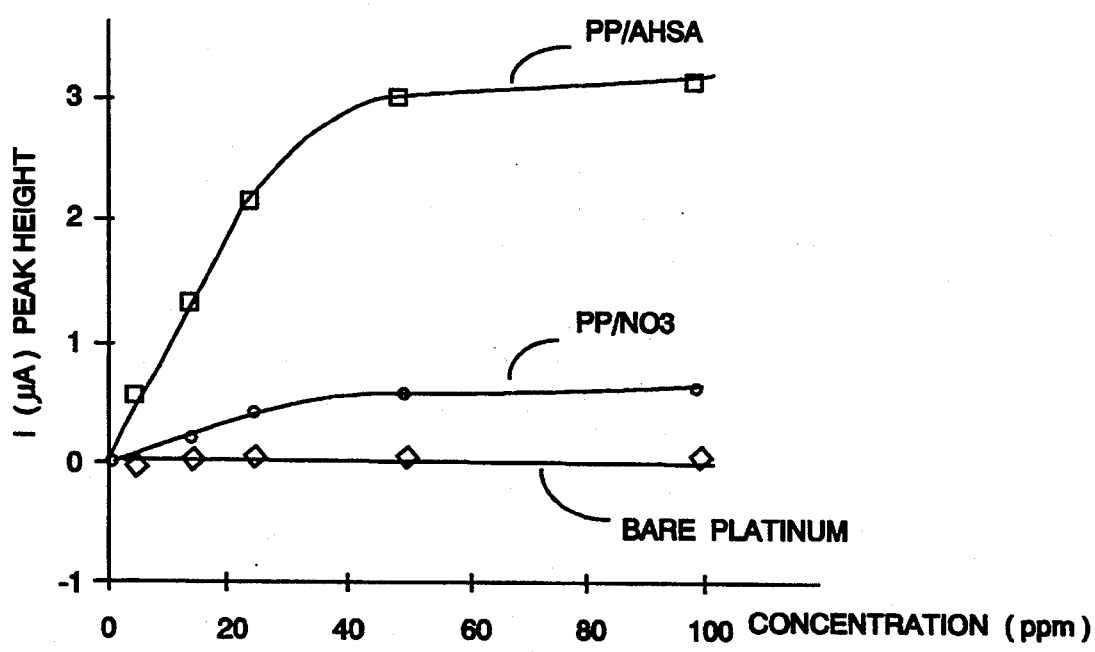
FIG. 13B is a calibration curve for the data shown in FIG. 13A.

For practical purposes, a 230 ms pulse width was used since doing so provided adequate sensitivity and resolution. Typical responses are shown in FIG. 13A, wherein the pulsed waveform has E1=+0.4 V, E2=0.00 V, t1 (or Ta)=120 ms, and t2 (or Tb)=120 ms. FIG. 13A compares injections of HSA at various concentrations. FIG. 13B shows calibration curves, wherein blank calibration curves on platinum and $PP/NO_3$ were also obtained to verify that the detected signal was in fact due to Ab-Ag interactions.

The reproducibility of the responses obtained was adequate (e.g., +5% over ten injections) in the range 5 ppm to 50 ppm protein, and the detection limit was about 0.5 ppm.

In summation, the above embodiment demonstrates that a rapid, sensitive and reproducible detection method for HSA using PP/AHSA with pulsed electrochemical detection in an flow injection analysis system has been realized. The described system overcomes many of the practical problems previously associated with direct electro-chemical immunoassay, and can be especially useful for other Ab-Ag systems.

Modifications and variations may be made to the disclosed embodiments without departing from the subject and spirit of the invention as defined by the following claims.

What is claimed is:

1. A method for detecting a target analyte within a solution, the method comprising the following steps:
   (a) exposing said solution to an electrode that includes a conducting electroactive polymer;
   (b) coupling a periodic alternating voltage to said electrode; and
   (c) measuring current flow through said electrode as a function of time and as a function of said alternating voltage to detect said target analyte within said solution;
   wherein a characteristic of said electrode is varied upon exposure to said target analyte, causing current flow through said electrode to vary.

2. The method of claim 1, wherein at step (b), said alternating voltage has a period that includes at least an oxidizing time interval during which said voltage causes said electrode to be oxidized, and a reduction time interval during which said voltage causes less oxidation or reduction or both to said electrode reduced.

3. The method of claim 2, wherein said alternating voltage has a duty cycle and period set to meet at least one criterion selected from the group consisting of (i) minimization of electrode fouling by an analyte, (ii) enhancement of electrode detection sensitivity to an analyte, (iii) enhancement of selectivity to a chosen target analyte group, (iv) enhancement of selectivity to a chosen target analyte, (v) reduction of hysteresis effect in detected data, and (vi) said periodic alternating voltage is asymmetrical.

4. The method of claim 2, wherein:
   said target analyte is an anion; and
   said target analyte reversibly attaches to said electrode during at least a portion of said oxidizing time interval.

5. The method of claim 2, wherein:
   said target analyte is a cation; and
   said target analyte reversibly attaches to said electrode during at least a portion of said reduction time interval.

6. The method of claim 1, wherein at step (c), said current flow includes at least one component selected from the group consisting of (i) a Faradaic current associated with application of said voltage, (ii) a current associated with a migration of said analyte to said electrode, and (iii) a counter current associated with migration to said electrode of an ion of charge opposite to said target analyte.

7. The method of claim 1, wherein at step (c), said voltage has at least one characteristic selected from the group consisting of (i) a voltage magnitude that varies from about +2 VDC to about −2 VDC in a single period; (ii) a period of about 50 ms to about 250 ms, (iii) a period that includes a first time interval ranging from about 10 ms to about 50 ms during which interval said voltage causes said electrode to oxidize, and (iv) a period that includes a second interval ranging from about 10 ms to about 50 ms during which interval said voltage causes said electrode to re-oxidize.

8. The method of claim 1, wherein said voltage has a waveform which reduces hysteresis in repetitive measurements of said current as a function of said voltage.

9. The method of claim 1, wherein said solution is selected from the group consisting of (i) a stream associated with an output from a flow injection analysis system, (ii) a stream associated with output from liquid chromatography, (iii) a stream associated with output from ion chromatography, and (iv) a stream associated with output from a capillary electrophoresis system.

10. A method for detecting a bindable target substance having an attachment affinity for an immobilized receptor, the method comprising the following steps:
    (i) (a) forming an electrode having an conducting electroactive polymer layer that includes an immobilized receptor will bind to a bindable target substance;
    (b) contacting said electrode with an aqueous solution including a bindable target substance;
    (c) coupling a periodic alternating voltage to said electrode; and
    (d) measuring current flow through said electrode as a function of time and as a function of said alternating voltage to determine whether attachment of said bindable target substance to said immobilized receptor has occurred;
    wherein at least one characteristic of said electrode is varied upon an attachment between said immobilized receptor and bindable target substance, causing current flow through said electrode to vary.

11. The method of claim 10, wherein said immobilized receptor is selected from the group consisting of (i) antibody, (ii) antigen, (iii) hapten, (iv) DNA, (v) RNA, and (vi) enzymes.

12. The method of claim 10, wherein at step (c), said alternating voltage has a period that includes at least an oxidizing time interval during which said voltage causes said electrode to be oxidized, and a reduction time interval during which said voltage causes less oxidation or reduction or both to said electrode reduced.

13. The method of claim 10, wherein said alternating voltage has a duty cycle and period set to meet at least one criterion selected from the group consisting of (i) minimization of electrode fouling, (ii) enhancement of electrode detection sensitivity, (iii) enhancement of selectivity, (iv) promote reversibility of attachment between said immobilized receptor and said bindable target substance, (v) reduction of hysteresis in repetitive measurements of said current as a function of said voltage, and (vi) said alternating voltage is asymmetrical.

14. The method of claim 10, wherein at step (d), said alternating voltage has at least one characteristic selected from the group consisting of (i) a voltage magnitude that varies from about +2 V to about −2 V in a single period; (ii) a period of about 50 ms to about 250 ms, (iii) a period that includes a oxidizing time interval ranging from about 10 ms to about 50 ms during which interval said voltage causes said electrode to oxidize, and (iv) a period that includes a reduction time interval ranging from about 10 ms to about 50 ms during which interval said voltage causes said electrode to re-oxidize.

15. The method of claim 10, wherein at step (b) said solution is selected from the group consisting of (i) a stream associated with an output from a flow injection analysis system, (ii) a stream associated with output from liquid chromatography, (iii) a stream associated with output from ion chromatography, and (iv) a stream associated with output from a capillary electrophoresis system.

* * * * *